(12) United States Patent
Mariani et al.

(10) Patent No.: US 6,627,799 B1
(45) Date of Patent: *Sep. 30, 2003

(54) PLANTS WITH MODIFIED STAMEN CELLS

(75) Inventors: Celestina Mariani, Heusden (BE); Jan Leemans, Deurle (BE); Willy De Greef, Ghent (BE); Marc De Beuckeleer, Merelbeke (BE)

(73) Assignee: Bayer BioScience NV, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 08/485,516

(22) Filed: Jun. 7, 1995

Related U.S. Application Data

(63) Continuation of application No. 08/027,580, filed on Mar. 5, 1993, now Pat. No. 6,372,967, which is a continuation of application No. 07/449,901, filed as application No. PCT/EP89/00495 on Apr. 27, 1989, now abandoned.

(30) Foreign Application Priority Data

Apr. 28, 1988 (GB) .............................. 8810120

(51) Int. Cl.⁷ ................. C12N 15/82; C12N 15/29; C12N 15/55; C12N 15/56; C12N 15/57; A01H 1/02; A01H 5/00; A01H 5/10

(52) U.S. Cl. ................ 800/303; 800/271; 800/274; 800/278; 800/279; 800/282; 800/287; 800/288; 800/289; 800/300; 800/302; 435/69.7; 435/69.8; 435/198; 435/199; 435/200; 435/209; 435/219; 435/320.1; 435/418; 435/419; 435/468

(58) Field of Search ............... 435/69.1, 70.1, 435/172.3, 240.4, 199, 200, 209, 219, 69.7, 69.8, 418, 419, 468, 320.1, 198; 800/205, 250, 271, 274, 278, 287, 288, 300, 279, 282, 289, 302, 303; 536/24.1, 23.71; 47/58

(56) References Cited

U.S. PATENT DOCUMENTS

| | | | |
|---|---|---|---|
| 3,842,538 A | 10/1974 | Barabas | 47/58 |
| 4,305,225 A | 12/1981 | Yuan | 47/58 |
| 4,351,130 A | 9/1982 | Rutger et al. | 47/58 |
| 4,407,956 A | 10/1983 | Howell | 435/172.3 |
| 4,517,763 A | 5/1985 | Beversdorf et al. | 47/58 |
| 4,536,475 A | 8/1985 | Anderson | 435/172.3 |
| 4,658,085 A | 4/1987 | Beversdorf et al. | 800/200 |
| 4,727,219 A | 2/1988 | Brar et al. | 800/200 |
| 5,356,799 A | 10/1994 | Fabijanski et al. | 435/172.3 |

FOREIGN PATENT DOCUMENTS

| | | |
|---|---|---|
| EP | 0 198 288 | 10/1986 |
| EP | 0 329 308 | 8/1990 |
| WO | 92/13956 | 8/1992 |
| WO | 92/13957 | 8/1992 |

OTHER PUBLICATIONS

Twell et al., *J. of Cellular Biochemistry*, Supp. 13D, p. 312, abstract M349 (1989).
Van Tunen et al., *J. of Cellular Biochemistry*, Supp. 13D, p. 292, Abstract M257 (1989).
Gasser et al., *J. of Cellular Biochemistry*, Supp. 12C, p. 137, Abstract L021 (1988).
Wing et al., *J. of Cellular Biochemistry*, Supp. 12C, p. 168, Abstract L137 (1988).
McCormick et al., *Biological Abstracts*, No. BR33:815569 (1986).
Goldberg, *Science*, vol. 240, pp. 1460–1467 (1988).
Medford et al., *J. of Cellular Biochemistry*, Supp. 12C, p. 212, Abstract L616 (1988).
Mascarenhas, *J. of Cellular Biocemistry*, Supp. 12C, p. 138, Abstract L023 (1988).
Kiesselbach, *The Structure and Reproduction of Corn*, University of Nebraska Press, Lincoln and London, pp. 40–49 (1980).
McCormick, et al., *Tomato Biotechnolgy*, pp. 255–265, 1987.
Kamaly, et al. *Proc. Natl. Acad. Sci.*, vol. 81, pp. 2801–2805, May 1984.
Rothstein, et al., *Proc. natl. Acad. Sci.*, vol. 84, pp. 8439–8443, Dec. 1987.
Grill, *Plant Molecular Biology Reporter*, vol. 1, No. 1, pp. 17–20, 1983.
Traynor, et al., *Plant Molecular Biology,*, vol. 7, pp. 255–263, 1986.
Turpen, et al., *Plant Molecular Biology*, vol. 10, pp. 489–498, 1988.
Murai, et al., *Science*, vol. 222, pp. 476–482, Nov. 1983.
Larkins, et al., *J. Cell. Biochem.*, Supp. O (9 part C): 264, No. 1818.
Shen et al., *Mol. Gen. Genet.*, vol. 234, pp. 379–389, 1992.
Koltnunow et al., *The Plant Cell*, vol. 2, pp. 1201–1224, 1990.
Winnacker, *From Genes to Clones*, pp. 401–404, VCH Verlaggesellschaft mbH, Weinheim, Germany.
Peacock, *Nature*, vol. 347, pp. 714–715, 1990.
Spena et al., *Theor. Appl. Genet*, vol. 84, pp. 520–527, 1992.
Mariani, et al., *Nature*, vol. 347, No. 6295, pp. 737–741, Oct. 25, 1990.
Smith, et al., *Nature*, vol. 334, pp. 724–726, Aug. 25, 1988.
Worrall, et al., *The Plant Cell*, vol. 4, pp. 759–711, Jul. 1992.
Chang et al., *Molecular and Cellular Biology*, vol. 5, No. 9, pp. 2341–2348, Sep. 1985.

(List continued on next page.)

*Primary Examiner*—David T. Fox
(74) *Attorney, Agent, or Firm*—Burns Doane, Swecker & Mathis, LLP

(57) ABSTRACT

A plant, the nuclear genome of which is transformed with a foreign DNA sequence encoding a product which selectively disrupts the metabolism, functioning and/or development of stamen cells of the plant. The foreign DNA sequence also optionally encodes a marker.

71 Claims, 21 Drawing Sheets

OTHER PUBLICATIONS

Evans, et al., *Biochemical Soceity Transactions*, pp. 334S, 1992.

Paul, et al., *Plant Molecular Biology*, vol. 19, pp. 611–622, 1992.

Sheehy, et al., *Proc. Natl. Acad. Sci.*, vol. 85, pp. 8805–8809, Dec. 1988.

Coghlan, *New Scientist*, Jul. 18, 1992, pp. 20.

Mauch, et al., *Plant Physiol.*, vol. 88, pp. 936–942, 1988.

Boller, Chapter 13, *Plant Response to Stress*, "Hydrolytic Enzymes in Plant Disease", pp. 385–413.

Weintraub, *Scientific American*, Jan. 1990, pp. 34–40.

van der Meer, et al., *The Plant Cell*, vol. 4, pp. 253–262, Mar. 1992.

Lamy, et al., *Nucleic Acids Research*, vol. 19, No. 5, pp. 1001–1005, Jan. 31, 1991.

FIG. 2

```
CAA TCC GCT AGA CTA TAC CGT TGC AAG CCA GGG CCA AAT ATG TGT GAC AGT AAA
 Q   S   A   R   L   Y   R   C   K   P   G   P   N   M   C   D   S   K    54

GAC TGT AAT GAG CTT CTC CTA CAC TTT GTT TTC CCA ATG CAA GAC AAA CAT GAC
 D   C   N   E   L   L   L   H   F   V   F   P   M   Q   D   K   H   D   108

AAT AAA CAA GAA CAT CTA AGA TAT GGA GGA CGC CGA ATG CAA GGT ATA CTC GTG
 N   K   Q   E   H   L   R   Y   G   G   R   R   M   Q   G   I   L   V   162

GGA GTT GGC GGT TTT GGA ATT GGA CGC TGG GGT GCT TGG GGT GGT GGT GGT GGC
 G   V   G   G   F   G   I   G   R   W   G   A   W   G   G   G   G   G   216

GGA GGT GGT GGT TCT GAT GCC CCT GGT AGT AAC GAT GGC TGT CCT GAC CCT GGC (?) 270

GGT TTT GGC TGT CCC CCG GGC GGC TGT TAT GCA TGT CCT GCC AAC AAT CCT AGT
 F   G   C   P   P   G   G   C   Y   A   C   P   A   N   N   P   S   324
                                                                       351

GGA GGA ATA ACT GAA TTC CAT ATC TCA GGA TTG GCA
 G   G   I   T   E   F   H   I   S   G   L   A
```

```
                ClaI
GTTTGACAGCTTATCATCGATTATATTAGGGATTTTTACACAAATAGCCGGCTATA           56
TTAATTGTTTACTTTTTCTAACCATATACATAGATTATACATTGATTATACATTAAT         126
ATATAAATTATGCATATAATATACATTCGCTGGTTATTTTTAGTTTAAGTTATACATTTAAGTTATAGGGTGGGAGGCTATT   196
GGATTAATTCTTTATTATATTAAATATTTACGAATTTCGTGTGTTGACGGTGTAAATCATATGTATTGATA             266
CTTGTTGCTTCTTTATTAATTTTAGTGATTTAGATTCCCTAGAAACTACCACCATATGCTGTTTTTAGGTTC             336
GTATAATATGAGAAAAGTTTATTTTAGTCGCTTCCAAATATATATTTATATACTTTCTCCGGTCCACAA               406
TAAGTGATTTTTGGTTGTTTCACACAGATTAAGAAATTCACATTTAACATTAAATAGCAATGAAATT                 476
GATCATATTAACCTTTACTATTTCTTCACATAAACATTTCTAACACATACTCCAACACCATTTACTCCAA               546
GGGCACTGTAGTAAAAAATAATTAAATCATTTTGAAATCTAAAAAACTCACTTATTTTGGACCATAAA                616
AAAAGGGCCAAAAATAACTTATTGTGACCGGAGAGTAATACACTTTTGGTTAGCGAATGCAATTA                   686
ATTTAGACATTGTGTTATGTTCCAGTTAACCGCTTCCCTGCACTTCTTCAATCTATCTCGATAGAAA                 756
ATTGTGATACTTTGCGACTTCTATCAGAGGACTTTTGTTTCCATGTAACAATCTGTCATTTCGATGG                 826
GGAGATTTGCACAAATAGGCTATTTATGTGATGGATATGTCCCAATTTAACCCCATGTCGATCAGAACTTAG            896
CCACGAGCACCAGAAGTTTGATGGATATCTAGCTAAGTATAACTGACTTTGTCACTATCCGGTTTACTAATCAAGAGCTATTTT   966
TATTCAAAATTGGATATCTAGCTAAGTATAACTGACTTTATGAAAGATGATTCAAACATGATTTTTTATGTACTAATATAT    1036
CAAGAAGGGACAATTGACTTGTCACTTATGAAAGATGATTCAAACATGATTTTTTATGTACTAATATAT              1106
ACATCCTACTCGAATTAAAGCGACATAGGCTCGAAGTATGCACATTTAGCAATGTAAATTAAATCAGTT              1176
TTGAATCAAGCTAAAAGCAGACTTGCATAAGGTGGGTGGCTGGACTAGAATAAACATCTTCTCTAGCACA             1246
```

FIG. 3A-1

```
GCTTCATAATGTAATTTCCATAACTGAAATCAGGGTGAGACAAAATTTGGTACTTTTCCTCACACTAA      1316
GTCCATGTTTGCAACAAATTAATACATGAAACCTTAATGTTACCCTCAGATTAGCCTGCTACTCCCCATT    1386
                                          *******
TTCCTCGAAATGCTCCAACAAAAGTTAGTTTTGCAAGTTGTTGTGTATGTCTTGTGCTCTATATGCCC      1456
         *                                            CTTTAATCGATTT
TTGTGGTGCAAGTGTAACAGTACAACATCATCACTCAAATCAAAGTTTTACTTAAAGAAATTAGCTAAA     1526
TACCATCGAGG                  HindIII
ATGGTAGCTCCAAAATGGGTTTTCATTTCTTTTATGATTTTGCTAAGCTTAGCAATATGCTCTGGCCAGC    1596
 M  V  A  P  K  W  V  F  I  S  F  M  I  L  L  S  L  A  I  C  S  G  Q  P
CTGTTACCTCTGATGCAATTAAGGCTAAGGAAGCTGATCATGACAACCTCAAAGCTCACACTCTGAGTAA    1666
 V  T  S  D  A  I  K  A  K  E  A  D  H  D  N  L  K  A  H  T  L  S  N
TATCGACGCCAAAGGCTTTGGAGGAGGCGGTGGATTTGGGGGATGGGCCGGTGGTGGTGGGGGTGGA       1736
 I  D  A  K  G  F  G  G  G  G  G  F  G  G  W  A  G  G  G  G  G
GGTGGTGGAGATGGTGGGGGTTCTGACACCCCTAACTACGGTTATAACCCTGGCTGCAGTATCCATGGTT    1806
 G  G  G  D  G  G  G  S  D  T  P  N  Y  G  Y  N  P  G  C  S  I  H  G  C
GCACTGTCCCTGGCTTTGGTTTCCTACCTAAACCTGTCTTTGGTGTCCCAGTCTATTCCCCTGGTTGTGG    1876
 T  V  P  G  F  G  F  L  P  K  P  V  F  G  V  P  V  Y  S  P  G  C  G
CTATGTGTGTCCGGCCGATATTCCTACTGGAGGAATGACTGAATCCAAAATCACAGGAATATCACAATCC   1945
 Y  V  C  P  A  D  I  P  T  G  G  M  T  E  S  K  I  T  G  I  S  Q  S
                            cDNA CLONE TA29 -->  ACAATCC
```

FIG. 3A-2

```
GCTAGACTATACCGTTGCAAGCCAGGGCCAAATATGTGTGACAGTAAAGACTGTAATGAGCTTCTCCTAC
GCTAGACTATACCGTTGCAAGCCAGGGCCAAATATGTGTGACAGTAAAGACTGTAATGAGCTTCTCCTAC  2016
 A  R  L  Y  R  C  K  P  G  P  N  M  C  D  S  K  D  C  N  E  L  L  L  H

ACTTTGTTTTCCCAATGCAAGACAAACATGACAATAAACAAGAACATCTAAGATATGGAGGACGCCGAGG
ACTTTGTTTTCCCAATGCAAGACAAACATGACAATAAACAAGAACATCTAAGATATGGAGGACGCCGAGG  2086
  F  V  F  P  M  Q  D  K  H  D  N  K  Q  E  H  L  R  Y  G  G  R  R  G

TATAGGTCTCACTGTGGGAGGAGTTGGCGGTTTTGGAATTGGTTTTGGTGCTTGGGGTGGTGGTGGTGGC
TATAGGTCTCACTGTGGGAGGAGTTGGCGGTTTTGGAATTGGTTTTGGTGCTTGGGGTGGTGGTGGTGGC  2156
  I  G  L  T  V  G  G  V  G  G  F  G  I  G  F  G  A  W  G  G  G  G

GGAGGAGGTGGTGGTTCTGATGCCCCTGGTTGTAGTAACGATGGCTGTGACCCTGGTTTTGGCTGTCCCC
GGAGGAGGTGGTGGTTCTGATGCCCCTGGTTGTAGTAACGATGGCTGTGACCCTGGTTTTGGCTGTCCCC  2226
  G  G  G  G  S  D  A  P  G  C  S  N  D  G  C  D  P  G  F  G  C  P  P
                                                        EcoRI
CGGGCTGTGGTTATGCATGTCCTGCCAACAATCCTAGTGGAGGAATAACTGAATTCCATATCTCAGGATT
CGGGCTGTGGTTATGCATGTCCTGCCAACAATCCTAGTGGAGGAATAACTGAATTCCATATCTCAGGATT  2296
  G  C  G  Y  A  C  P  A  N  N  P  S  G  G  I  T  E  F  H  I  S  G  L

<-- end cDNA clone TA29
ATCACGATTCGATGGACCTTACAGATGTAGGCCAGATATGTGTGAAAGTGAAGATTGTAATGAACTTCTT  2366
 S  R  F  D  G  P  Y  R  C  R  P  D  M  C  E  S  E  D  C  N  E  L  L CTACACTTTGTTTCTCCAATGCAACACAAACATGAGAACCGACATGATCATATAGTAGAAAGGAGTGATG  2436
 L  H  F  V  S  P  M  Q  H  K  H  E  N  R  H  D  H  I  V  E  R  S  D  E AGGAGGAAGCGCATCATCAGTCAAAGCAGCATAAAGACGAAGACATCATAAACTAGGCTCTCCCACAAAC  2506
 E  E  A  H  H  Q  S  K  Q  H  K  D  E  D  I  I  N  *

CAAAAAAAAGGAACTATATATGTAGCTTCAGCCAAAAAACTGTATACACTGTCTAAGAATACTCACTTC  2576

CAACGAACTTAAATAAAACTAGTTTACAGTGGATTGGGATATAATCAGTTGGACAATTTGCTAAACCTCC  2646

TCATGCACTGTAAAAATAGACTTGCTACTAGTATTTGGAATATAATGCTGAATATATTTGTTGTTACTTT  2716

GCCTAATGTCAATCAGCATTCAGCAATTTCTCTGTAGTTAGAAAATGAAAGGAAGAATCAGGAAACTCAT  2786

ATTTAAAGGATGAAATAATTTAAAGATCGCGAAGCAGTCACAATTTAATAGTACCAGGAAAATAATCTAT  2856

AGGAATCACAGAACTTTTTGATTTATCAAATTAAGGAAGCAAACTGGGAAAATGTGAAATGAATGAACAT  2926

AATGCTGAAAGCTATTGATCAGATGATTGGATTGATTTCGTAGGAGCAACATATGATTTAAGATTATTTC  2996

AACAAGATGGCCATAAAGTAGCATATCATTTGTAATTTAACATTATTACACTCAAACTCAGGAAGATTGT  3066

CAATTTACCCTCAAAACAAAGTTTTAAGCCTTCAGTCTCCTTCAACCACAGTGGCACCTGCCCAATTGGC  3136

AGCACTTCCCCGGCGTGGAATGCTGTGGAGTTTGGTGTACAAATCCACCTGGAAAATCACAGCATTGATG  3206
                                                        HindIII
TTTCCTTCATCATGTTCGCGTGCAATTGCTTTTACTTTGTGCAGTGGATGATCAAAGCTT  3266
```

FIG. 3A-3

1    aaagtctttacttaaagaaattagctaaaatggtagctccaaaatggtctttcatttcttttatgattttgc
73   taagcttagcaatatgctctggccagcctgttacctttgatgcaattaaggctaaggaagctgatcatgaca
145  acctcaaagctcacactctaagtaatatcgacaccaaaggctttggaggaggcggtggatttggcattggtg
217  gtgtttgggccggaggtggtggtggtggtggttctgacgcccctaactacggttataaccctggctgcagta
289  tccgtggttgcactgtccctggctttggtttcctacctaatcctggttttggtgttccagtctattcccctg
361  gttgtggctatgtgtgtccagccgatatttctgctgaaggaatgactgaatccaaaatcacaggaatatcAg
                                                                              |
                                                                              |
                                                                              Ac
1
433  AATCgGCTAGACcATAtCGaTGCAgGCCtGGGgCAAATATGTGTGgCAGTAAAGAtTGTAATGAGCTTCTCC
     |||| ||||||| ||| || |||| ||| ||| ||| ||||||||||||| |||||||| |||||||||||||
     |||| ||||||| ||| || |||| ||| ||| ||| ||||||||||||| |||||||| |||||||||||||
3    AATCcGCTAGACtATAcCGtTGCAaGCCaGGGcCAAATATGTGTGaCAGTAAAGAcTGTAATGAGCTTCTCC 505  TACACTTTGTTTTCCCcATGCAAGACAAACATGAgAATAAACAAGAAtATCTAAGATATGGAGGACGtCGAG
     |||||||||||||||| |||||||||||||||| |||||||||||| |||||||||||||||||||| ||||
     |||||||||||||||| |||||||||||||||| |||||||||||| |||||||||||||||||||| ||||
75   TACACTTTGTTTTCCCaATGCAAGACAAACATGAcAATAAACAAGAAcATCTAAGATATGGAGGACGcCGAG 577  GTATAGGTCTCAgTGTGaGtGaAtcTaGtGGTTTTGGAATTGGTTTTGGTGCTcggggTGGTGGTGGTGGcG
     ||||||||||| ||||| | | |  | | ||||||||||||||||||||||||    | |||||||| | 
     ||||||||||| ||||| | | |  | | ||||||||||||||||||||||||
147  GTATAGGTCTCAcTGTGgGaGgAgtTgGcGGTTTTGGAATTGGTTTTGGTGCT    tGgGGTGGTGGTGGtG 649  GCGGAGGAGGgGGTGaTTCTaATGCCCCTGGCtTtGaTAtCcccGGaTtTaACCCcGGcTTTGGCTGTCCCt
     |||||||||| ||||| |||| |||||||||| | ||| | ||| | | | ||| || ||||||||||||| 
     |||||||||| ||||| |||| |||||||||| | ||| | ||| | | | ||| || |||||||||||||
216  GCGGAGGAGGtGGTGgTTCTgATGCCCCTGGtTgTagTAaCgatGGcTgTgACCCtGGtTTTGGCTGTCCCc 721  CGGGCTGTGGTTATGCATGTCCTGCCAACAATCCTAGTGGAGGAATAACTGAATTCCATATCTCAGGATTaT
     |||||||||||||||||||||||||||||||||||||||||||||||||||||||||||||||||||||| |
     |||||||||||||||||||||||||||||||||||||||||||||||||||||||||||||||||||||| |
288  CGGGCTGTGGTTATGCATGTCCTGCCAACAATCCTAGTGGAGGAATAACTGAATTCCATATCTCAGGATTgT 793  cacgAaacaatggaccttacagatgtaggccagatatgtgtgagagtgaagattgtaatgaacttctactac
         |
         |
360  tggcAg
865  actttgtttctccaaagcaacacaaacacgagaaccgacatgatcatacagtagaaagaaatgaagaggagg
937  aagctcatcatcagtcaaagcatcataaagacgaagacatcataaactag

FIG. 3B

```
          10         20         30         40         50         60         70
CGCAGGGGGG GGGGGGGGGG GATGTCAATA ACTTCCAAGT TCTTGCTAGT TATGTCCCTA
          80         90        100        110        120        130        140
GGACTAATAG TTTTTACCAC ATTTTCACTT GCTGATCAAC ACTACCAAATC TACCAAACAT GAGCTTGGAC
         150        160        170        180        190        200        210
GTTCTGATAC TAATCAGCTA AACATGAATG GTTACTTAGC CATGGAACAT GCACCACCAG ACCTTGAGCA
         220        230        240        250        260        270        280
AGAAGGGCAT ATGTGGCGCT TGAACGACGA CTCGATCGCC ATGGAACCAG CACCACCAGA CCTTGAGCAA
         290        300        310        320        330        340        350
GAAGTGCATA TGTGGCGCTT GAACGACGAC TCGATCGCCA TGGAACCAGC ACCAAGGTTT GAGCTAGAAG
         360        370        380        390        400        410        420
GGCAGAAGCA ACATGAGCAT GAGTCACACT TGAGGCTAGT AACTTAGAGAA ACATGATTAG CACCAGAATA
         430        440        450        460        470        480        490
GAATTAACTT GGAAGATGGT GGATTATTGT ACTATAGTCC CTTATTCTAA GTTGTGGATC AATAATAAAG
         500        510        520        530        540        550        560
CTCCATTGTC CTAAATTTCC ATCTGAGTTA AATTATCACC TTATAATTAA GTACCCCCCC CCCCCCCCCC
```

FIG. 3C

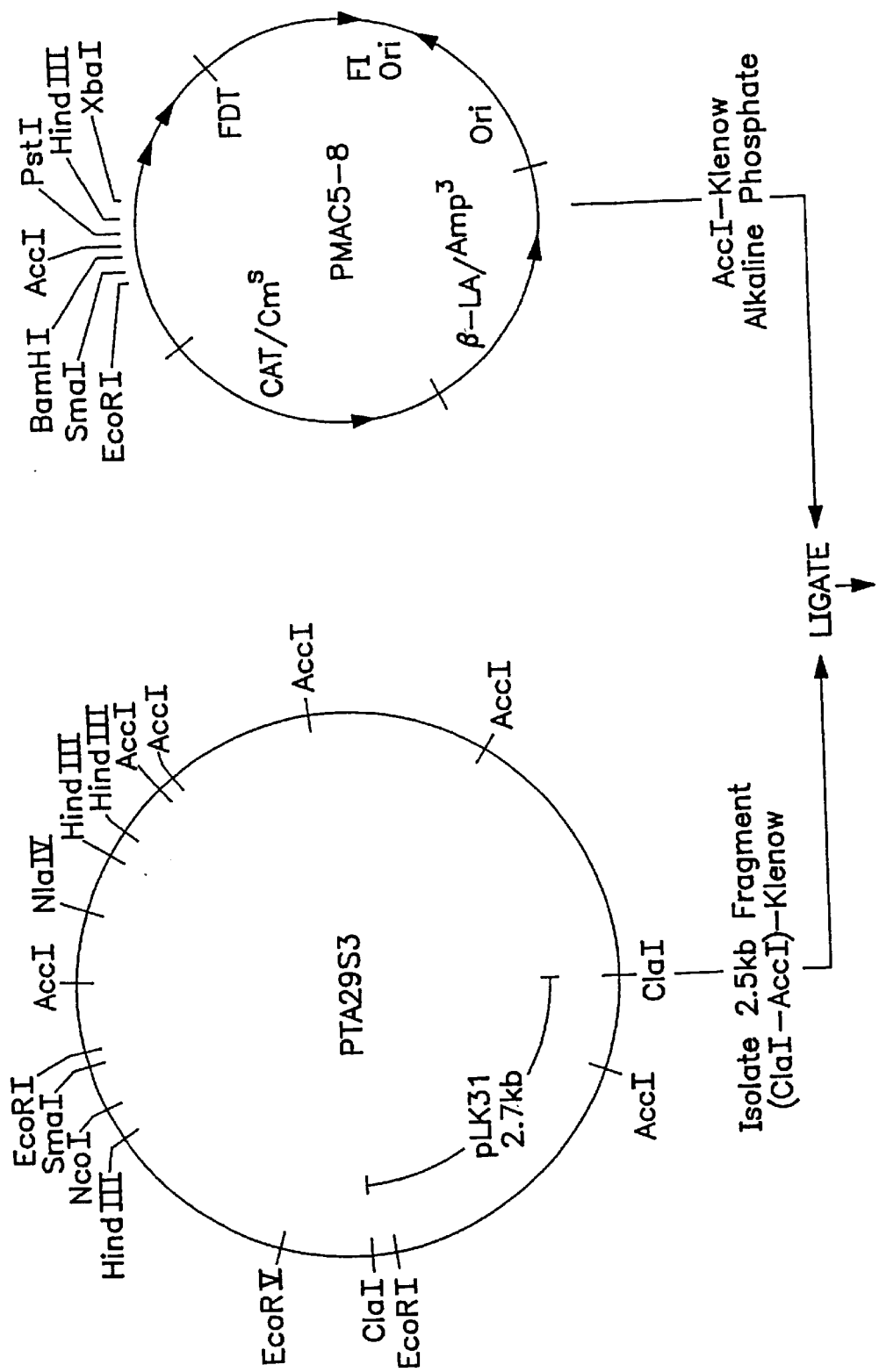
FIG. 4A-I

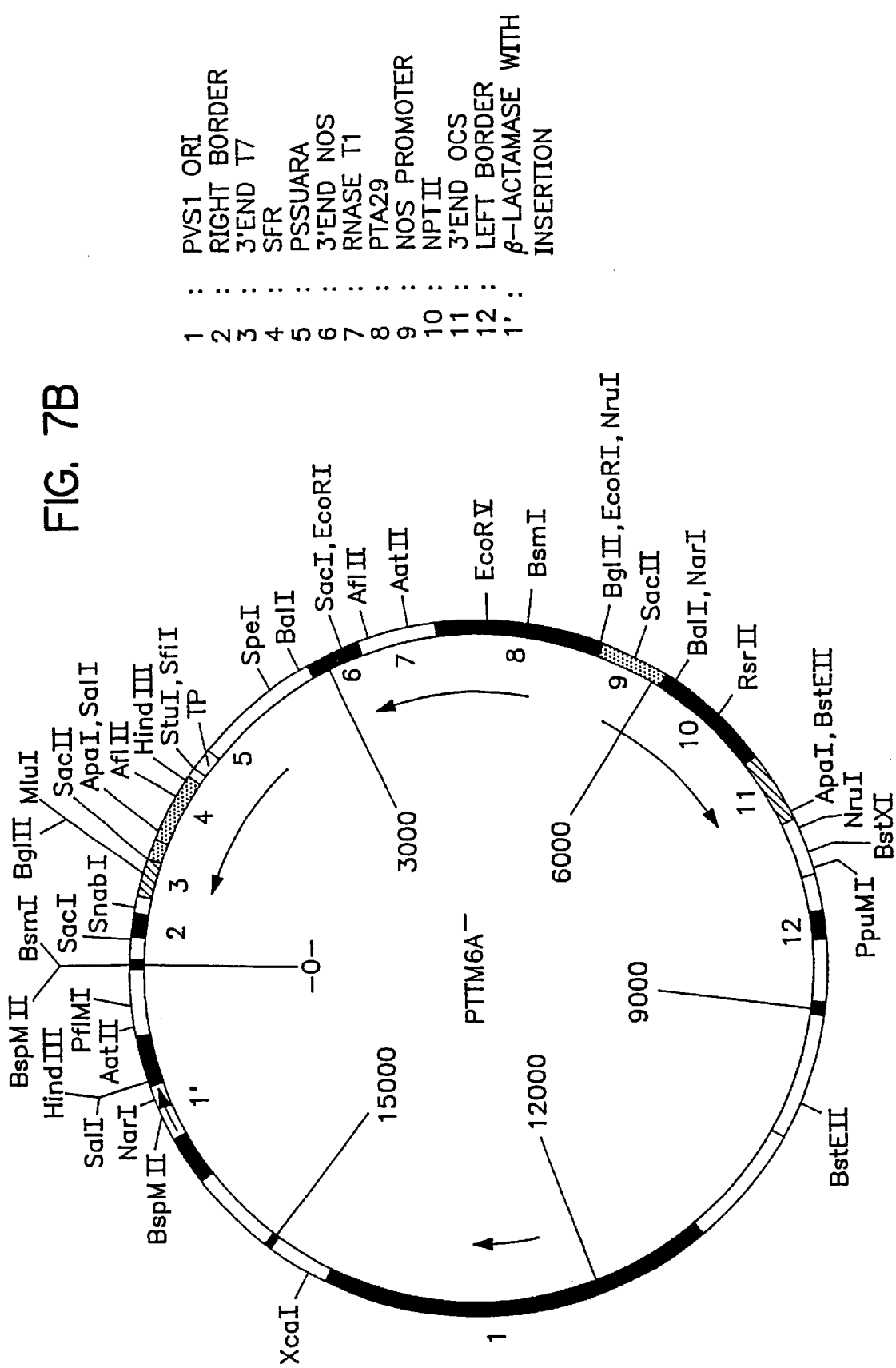

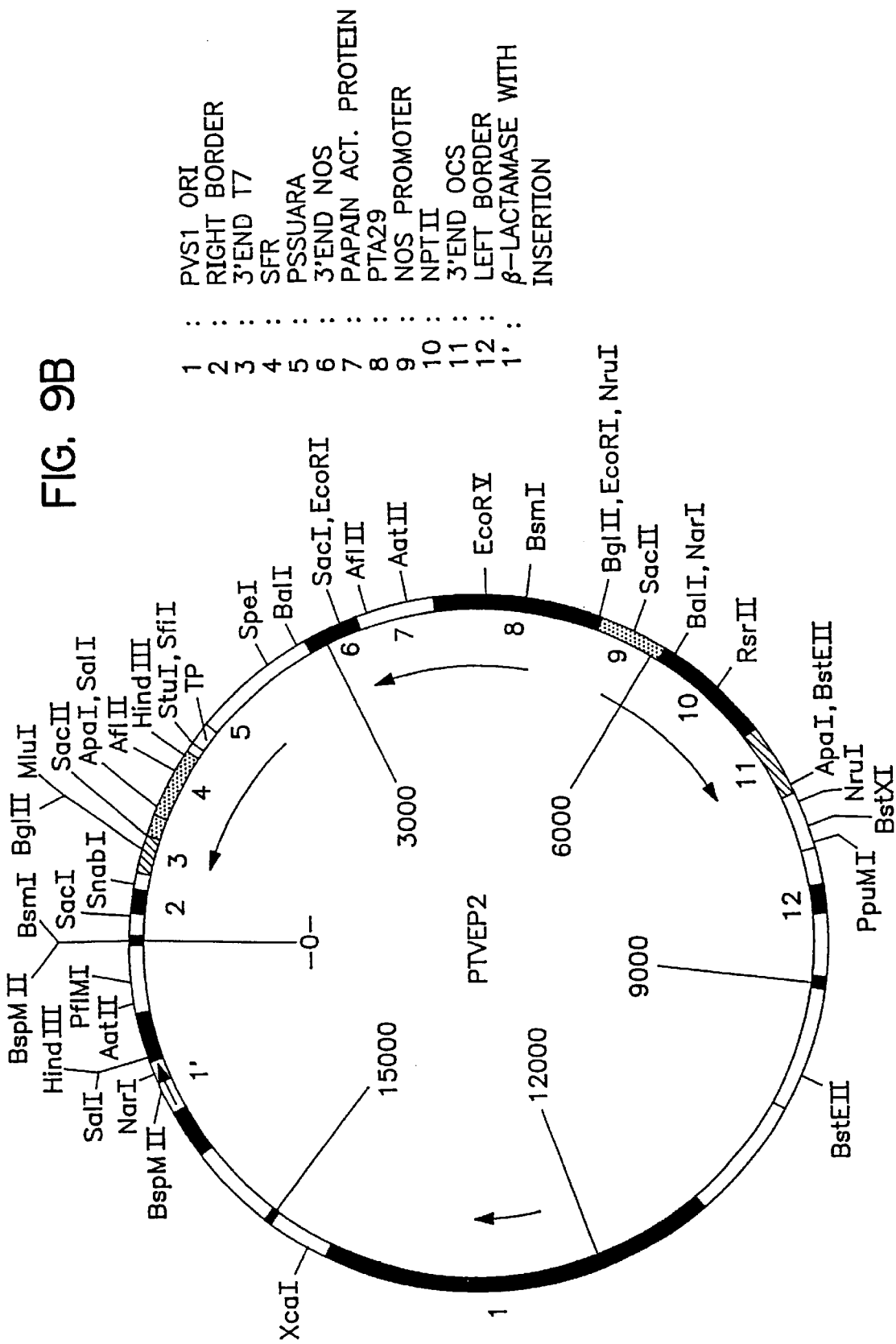

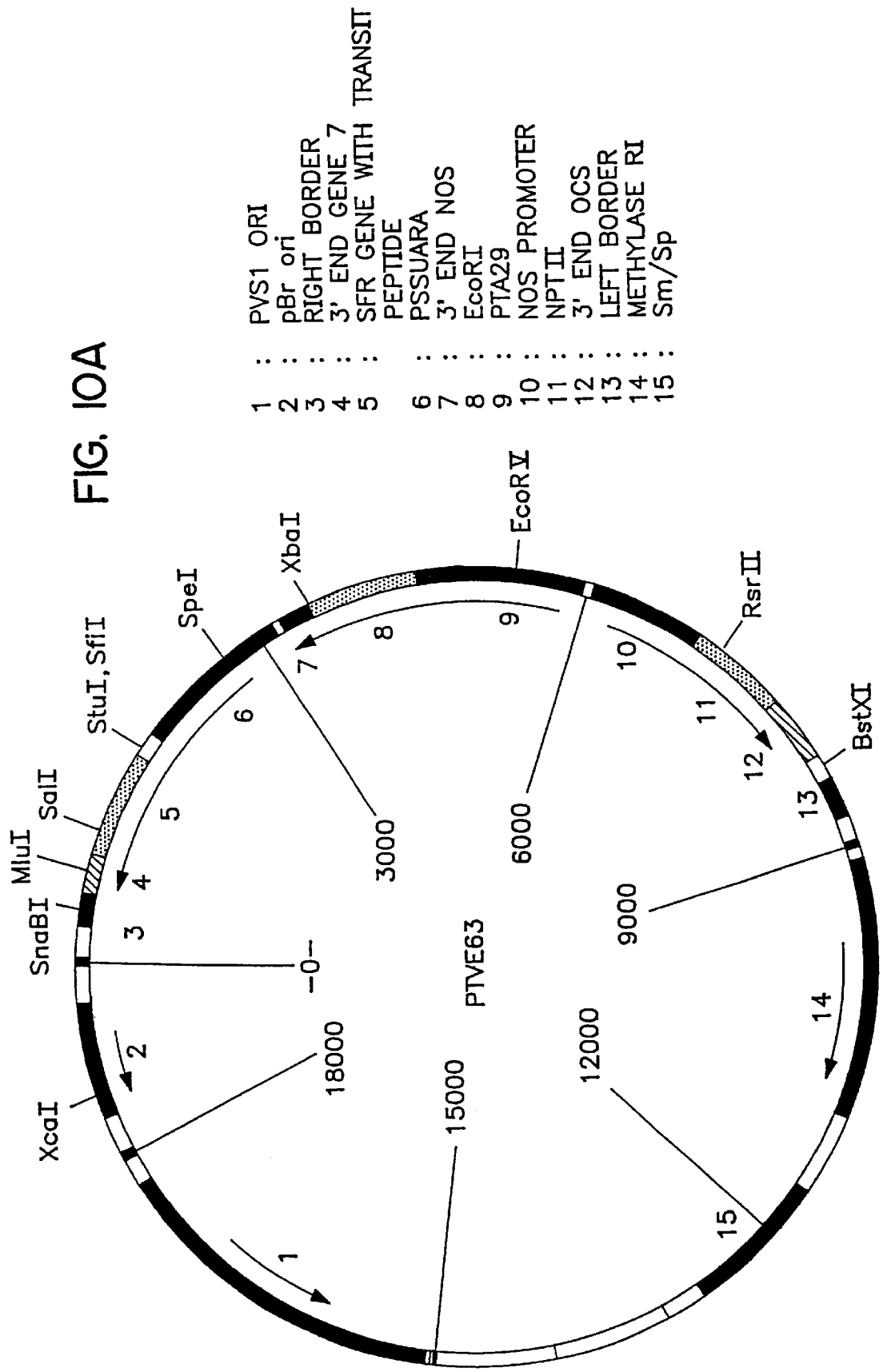

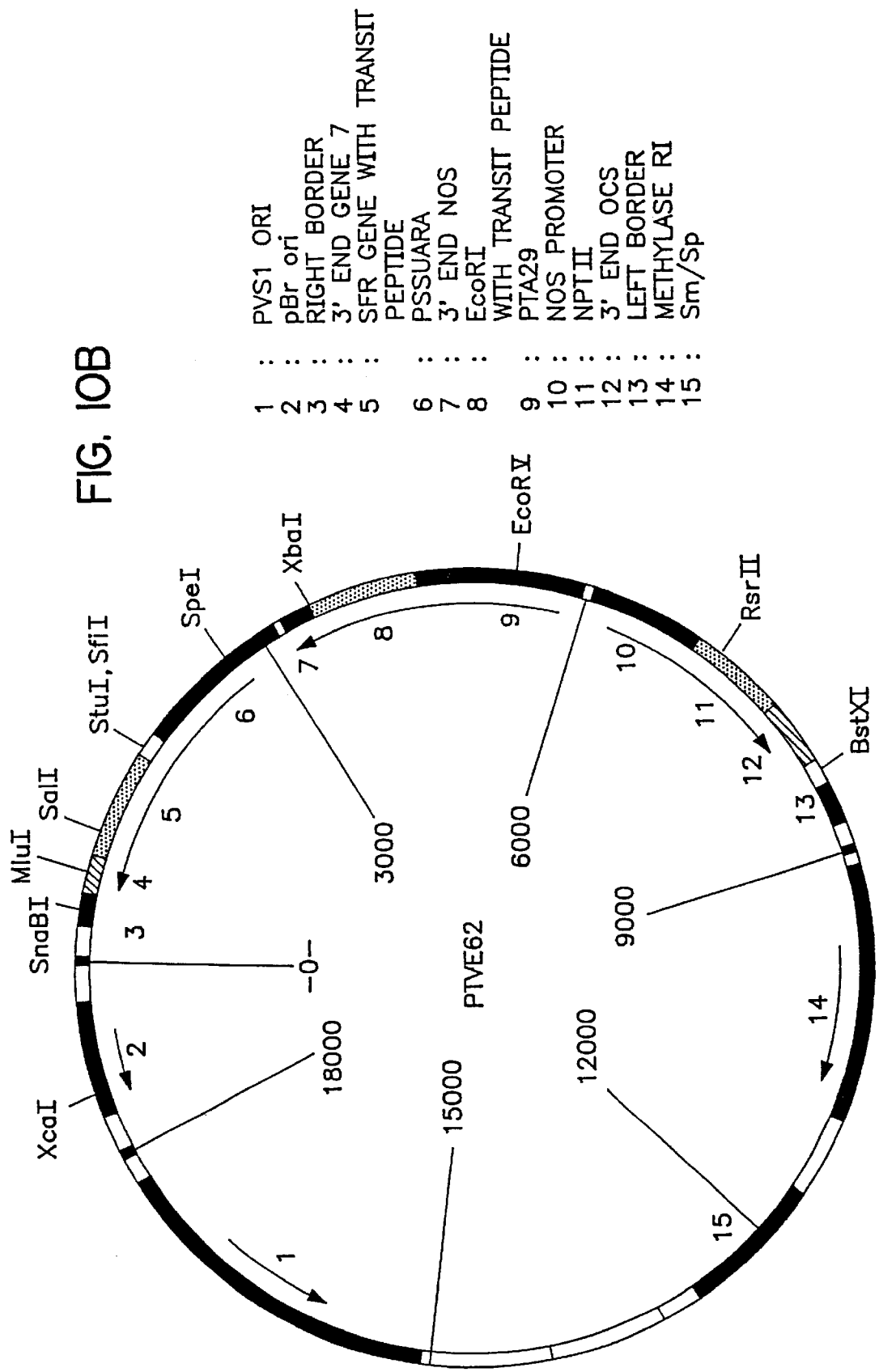

SR1 STAGE 1, ANTHER CROSS SECTION, THICK TAPETUM AROUND POLLEN SAC, POLLEN SAC: TETRAD FORM, X250 D.F.

N104 - 108 STAGE 1, ANTHER CROSS SECTION, THIN LAYER OF TAPETUM, NO POLLEN SAC, NO POLLEN VISIBLE, X250 D.F.

PLANTS WITH MODIFIED STAMEN CELLS

This application is a continuation, divisional, of application Ser. No. 08/027,580, filed Mar. 5, 1993; now U.S. Pat. No. 6,372,967; which is a continuation of application Ser. No. 07/449,901, filed Nov. 22, 1989, now abandoned which is a 371 PCT/EP89/00495 filed Apr. 27, 1989.

FIELD OF THE INVENTION

This invention relates to a male-sterile plant and to its reproduction material (e.g., seeds), in which the cells are transformed so that a foreign DNA sequence is stably integrated into their nuclear genome. The foreign DNA sequence of this invention contains at least one first foreign DNA (hereinafter the "male-sterility DNA") that: 1) sequence a first RNA or protein or polypeptide which, when produced or overproduced in a stamen cell of the plant, disturbs significantly the metabolism, functioning and/or development of the stamen cell; and 2) is in the same transcriptional unit as, and under the control of, a first promoter which is capable of directing expression of the male-sterility DNA selectively in stamen cells of the plant. In particular, this invention relates to such a nuclear male-sterile plant and its reproduction material, in which the foreign DNA sequence of this invention is a foreign chimaeric DNA sequence that can also contain at least one second foreign DNA (the "marker DNA") that: 1) encodes a second RNA or protein or polypeptide which, when present at least in a specific tissue or specific cells of the plant, renders the entire plant easily separable from other plants that do not contain the second RNA, protein or polypeptide at least in the specific tissue or specific cells; 2) is in the same transcriptional unit as, and under the control of, a second promoter which is capable of directing expression of the marker DNA in at least the specific tissue or the specific cells of the plant; and 3) is in the same genetic locus of the nuclear genome of the cells of the plant as the male-sterility DNA.

This invention also relates to a foreign chimaeric DNA sequence that contains at least one male-sterility DNA under the control of the first promoter and that can also contain, adjacent to the male-sterility DNA, at least one marker DNA under the control of the second promoter.

This invention further relates to a vector that contains the foreign DNA sequence of this invention and is suitable for the transformation of plant cells, whereby the foreign DNA sequence is stably integrated into the nuclear genome of the cells.

This invention still further relates to cells of a plant and to plant cell cultures, the nuclear genomes of which are transformed with the foreign DNA sequence.

This invention yet further relates to a process for producing a nuclear male-sterile plant and its reproduction material and its cell cultures containing the foreign DNA sequence in which the male-sterility DNA: 1) is under the control of the first promoter and optionally in the same genetic locus as the marker DNA under the control of the second promoter; 2) is stably integrated into the nuclear genome of the plant's cells; and 3) can be expressed selectively in stamen cells of the plant in the form of the first RNA, protein or polypeptide.

The invention further relates to a process for producing hybrid seeds, which grow into hybrid plants, by crossing: 1) the male-sterile plant of this invention which includes, in its nuclear genome, the marker DNA, preferably encoding a protein conferring a resistance to a herbicide on the plant; and 2) a male-fertile plant without the marker DNA in its genome. This invention particularly relates to such a process for producing hybrid seeds on a commercial scale, preferably in a substantially random population, without the need for extensive hand-labor.

This invention still further relates to a tapetum-specific promoter from a plant genome. This promoter can be used as the first promoter in the foreign DNA sequence of this invention for transforming the plant to render it nuclear male-sterile.

BACKGROUND OF THE INVENTION

Hybridization of plants is recognized as an important process for producing offspring having a combination of the desirable traits of the parent plants. The resulting hybrid offspring often have the ability to outperform the parents in different traits, such as in yield, adaptability to environmental changes, and disease resistance. This ability is called "heterosis" or "hybrid vigor". As a result, hybridization has been used extensively for improving major crops, such as corn, sugarbeet and sunflower. For a number of reasons, primarily related to the fact that most plants are capable of undergoing both self-pollination and cross-pollination, the controlled cross-pollination of plants without significant self-pollination, to produce a harvest of hybrid seeds, has been difficult to achieve on a commercial scale.

In nature, the vast majority of crop plants produce male and female reproductive organs on the same plant, usually in close proximity to one another in the same flower. This favors self-pollination. Some plants, however, are exceptions as a result of the particular morphology of their reproductive organs which favors cross-pollination. These plants produce hybrid offspring with improved vigor and adaptability. One such morphology in *Cannabis ssp.* (hemp) involves male and female reproduction organs on separate plants. Another such morphology in *Zea mays* (corn) involves male and female reproductive organs on different parts of the same plant. Another such morphology in *Elaeis guineensis* (oilpalm) involves male and fertile female gametes which become fertile at different times in the plant's development.

Some other plant species, such as *Ananas comosus* (pineapple), favor cross-pollination through the particular physiology of their reproductive organs. Such plants have developed a so-called "self-incompatibility system" whereby the pollen of one plant is not able to fertilize the female gamete of the same plant or of another plant with the same genotype.

Some other plant species favor cross-pollination by naturally displaying the so-called genomic characteristic of "male sterility". By this characteristic, the plants' anthers degenerate before pollen, produced by the anthers, reach maturity. See: "Male-Sterility in Higher Plants", M. L. H. Kaul, 1987, in: Monographs on Theoretical and Applied Genetics 10, Edit. Springer Verlag. Such a natural male-sterility characteristic is believed to result from a wide range of natural mutations, most often involving recessive deficiencies, and this characteristic can not easily be maintained in plant species that predominantly self-pollinate, since under natural conditions, no seeds will be produced.

There are four main types of male sterility observed in nature. All four types of male sterility are used in commercial breeding programs to ensure that there is cross-pollination to produce hybrid seed for crops such as corn, sugarbeet, oilseed rape and sunflower.

One type of male sterility is nuclear encoded and is believed to be inherited as a recessive allele. For breeding purposes, a recessive male-sterile parent plant is maintained by crossing it with a heterozygous male-fertile plant that also includes the recessive male-sterility allele, so that the offspring are 50% recessive male-sterile plants. The other 50% are male-fertile plants that have to be rogued out in outcrossing programs which can only be done efficiently if the recessive male-sterility allele is segregated together with a selectable or screenable marker. In U.S. Pat. No. 4,727,219, a procedure is described for the use of recessive male sterility for the production of hybrid maize.

A second type of male sterility is nuclear encoded but inherited as a dominant allele. An advantage of dominant male sterile plants, as compared to recessive male sterile plants, is that the dominant male-sterile plants can be maintained through crossing with a male-fertile plant, to produce offspring that are 50% dominant male-sterile plants. The usefulness of this dominant nuclear male-sterile plant is, however, limited because its dominant male-sterility allele is in most cases not tightly linked (i.e., within the same genetic locus) to a selectable or screenable marker.

A third type of male sterility is cytoplasmatically encoded. In most cases, the cytoplasmic code is in the mitochondrial genome of the plant, and only in a few cases is the code in the chloroplast genome of the plant. The inheritance of cytoplasmatically encoded male sterility does not follow Mendelian rules but rather depends on cytoplasmic factors. The offspring obtained from crosses between cytoplasmic male-sterile plants and male-fertile plants all carry the cytoplasmic male-sterility gene and are therefore sterile. As a result, the offspring of plants of this type are only of commercial value if the economic product of the offspring is not for use as seed but rather for plants such as ornamentals and sugarbeet.

A fourth type of male sterility is the result of a combination of both nuclear encoded male sterility and cytoplasmatically encoded male sterility. The male sterility-inducing nuclear alleles are usually recessive, and only plants that contain the male-sterility cytoplasmic allele and that are homozygous for the male sterility-inducing nuclear allele are phenotypically male sterile. In this type of plant, corresponding dominant male fertility-inducing alleles or "restorers of fertility", produce a male-fertile phenotype. As a result, the male-sterile offspring of this type of plant can be made male-fertile by pollinating the male-sterile plants with pollen containing the restorers of fertility. As a result, the offspring of plants of this type are of commercial value where the economic product is seed, that is for plants such as corn, sorghum and sunflower.

Typically, hybrid seed production has been accomplished by the large scale planting of cytoplasmic male-sterile plants and male-fertile plants and by somehow (e.g., with a distinctive marker) preventing the resulting hybrid seeds from becoming mixed with non-hybrid seeds. According to U.S. Pat. No. 3,842,538, hybrid seeds are tediously separated from non-hybrid seeds on the basis of color. According to U.S. Pat. No. 4,351,130, the problem of separating hybrid seeds from non-hybrid seeds is avoided by using short male-sterile plants and tall male-fertile plants and then destroying the tall male-fertile plants after pollination. According to U.S. Pat. Nos. 4,658,085, 4,517,763 and 4,658,084, cytoplasmic male-sterile plants are provided with a herbicide tolerance absent from the male-fertile plants which are destroyed with the herbicide after pollination. According to U.S. Pat. No. 4,305,225, male-sterile rice plants are sprayed with a growth hormone (e.g., gibberellin) in order to cause fuller emergence of flower-bearing panicles from rice leaf sheaths, thereby increasing the ability of the flowers to receive pollen from male-fertile plants.

In all such processes for producing hybrid seeds from male-sterile plants, ways have been sought for simply and inexpensively obtaining on a commercial scale: 1) high hybrid seed production from each male-sterile plant; 2) a hybrid seed population that results almost exclusively from pollen of male-fertile plants and eggs of male-sterile plants and is substantially free of non-hybrid seeds from male-fertile plants; 3) easy production of both the male-sterile and male-fertile plants; and 4) the virtually complete removal or destruction of either the male-fertile plants after they have pollinated the male-sterile plants or the selective separation of non-hybrid seeds, produced by the male-fertile plants, from the hybrid seeds produced by the male-sterile plants.

SUMMARY OF THE INVENTION

In accordance with this invention, a cell of a plant is provided, in which the nuclear genome is transformed with a foreign DNA sequence, preferably a foreign chimaeric DNA sequence, characterized by:

(a) a male-sterility DNA encoding a first RNA, protein or polypeptide which, when produced or overproduced in a stamen cell of the plant, disturbs significantly the metabolism, functioning and/or development of the stamen cell; and (b) a first promoter capable of directing expression of the male-sterility DNA selectively in stamen cells of the plant; the male-sterility DNA being in the same transcriptional unit as, and under the control of, the first promoter.

The foreign DNA sequence in the nuclear genome of the transformed cell can also comprise, preferably in the same genetic locus as the male-sterility DNA:

(c) a marker DNA encoding a second RNA, protein or polypeptide which, when present at least in a specific tissue or specific cells of the plant, renders the plant easily separable from other plants which do not contain the second RNA, protein or polypeptide at least in the specific tissue or specific cells; and (d) a second promoter capable of directing expression of the marker DNA at least in the specific tissue or specific cells; the marker DNA being in the same transcriptional unit as, and under the control of, the second promoter.

Also in accordance with this invention is provided a foreign chimaeric DNA sequence that comprises the male-sterility DNA and the first promoter and that can also comprise the marker DNA and the second promoter, as well as at least one additional DNA encoding a transit peptide capable of transporting the first protein or polypeptide or the second protein or polypeptide into a chloroplast or mitochondria of a plant cell in which the foreign chimaeric DNA sequence is expressed in its cytoplasm.

Further in accordance with this invention are provided: a male-sterile plant and a plant cell culture, each consisting of the transformed cells; a seed of the male-sterile plant; hybrid seeds and plants produced by crossing the male-sterile plant with a male-fertile plant; and a process for producing such hybrid seeds.

Still further in accordance with this invention are provided tapetum-specific first promoters.

DETAILED DESCRIPTION OF THE INVENTION

In accordance with this invention, a male-sterile plant is produced from a single cell of a plant by transforming the plant cell in a well known manner to stably insert, into the nuclear genome of the cell, the foreign DNA sequence of this invention. The foreign DNA sequence comprises at least one male-sterility DNA that is under the control of, and fused at its 5' end to, the first promoter and is fused at its 3' end to suitable transcription regulation signals (including a polyadenylation signal). Thereby, the first RNA, protein or polypeptide is produced or overproduced selectively in stamen cells of the plant so as to render the plant male-sterile. Preferably, the foreign DNA sequence also comprises at least one marker DNA that is under the control of, and is fused at its 5' end to, the second promoter and is fused at its 3' end to suitable transcription regulation signals (including a polyadenylation signal). The marker DNA is preferably in the same genetic locus as the male-sterility, whereby the second RNA, protein or polypeptide is produced in at least the specific tissue or specific cells of the plant so that the plant can be easily distinguished and/or separated from other plants that do not contain the second RNA, protein or polypeptide in the specific tissue or specific cells. This guarantees, with a high degree of certainty, the joint segregation of both the male-sterility DNA and the marker DNA into offspring of the plant.

The cell of a plant (particularly a plant capable of being infected with Agrobacterium) is preferably transformed in accordance with this invention, using a vector that is a disarmed Ti-plasmid containing the foreign DNA sequence and carried by Agrobacterium. This transformation can be carried out using procedures described, for example, in European patent publications 0,116,718 and 0,270,822. Preferred Ti-plasmid vectors contain the foreign DNA sequence between the border sequences, or at least located to the left of the right border sequence, of the T-DNA of the Ti-plasmid. Of course, other types of vectors can be used to transform the plant cell, using procedures such as direct gene transfer (as described, for example, in European patent publication 0,223,247), pollen mediated transformation (as described, for example, in European patent publication 0,270,356, PCT publication WO85/01856, and European patent publication 0,275,069), in vitro protoplast transformation (as described, for example, in U.S. Pat. No. 4,684,611), plant RNA virus-mediated transformation (as described, for example, in European patent publication 0,067,553, and U.S. Pat. No. 4,407,956) and liposome-mediated transformation (as described, for example, in U.S. Pat. No. 4,536,475).

Preferably, a nuclear male-sterile plant of this invention is provided by transforming a plant cell with a disarmed Ti-plasmid vector containing the foreign DNA sequence with both a male-sterility DNA under the control of a first promoter and a marker DNA under the control of a second promoter. The marker DNA can be upstream or downstream of the male-sterility DNA in the Ti-plasmid vector, but preferably, the two are adjacent to one another and are located between the border sequences or at least located to the left of the right border sequence of the Ti-plasmid vector, so that they are properly transferred together into the nuclear genome of the plant cell. However, if desired, the cell can initially be transformed with a foreign DNA sequence containing a male-sterility DNA and a first promoter and can subsequently be transformed with a marker DNA and a second promoter, inserted into the same genetic locus in the cell's nuclear genome as the male-sterility DNA. Suitable vectors for this purpose are the same as those discussed above for transforming cells with the foreign DNA sequence. The preferred vector is a disarmed Ti-plasmid vector.

The selection of the male-sterility DNA is not critical. A suitable male-sterility DNA can be selected and isolated in a well-known manner, so that it encodes the first RNA, protein or polypeptide which significantly disturbs the proper metabolism, functioning and/or development of any stamen cell in which the male-sterility DNA is expressed, preferably leading thereby to the death of any such stamen cell. Preferred examples of male-sterility DNAs encode: RNases such as RNase T1 (which degrades RNA molecules by hydrolyzing the bond after any guanine residue) and Barnase; DNases such as an endonuclease (e.g., EcoRI); or proteases such as a papain (e.g., papain zymogen and papain active protein).

Other examples of male-sterility DNAs encode enzymes which catalyze the synthesis of phytohormones, such as: isopentenyl transferase which is an enzyme that catalyzes the first step in cytokinin biosynthesis and is encoded by gene 4 of Agrobacterium T-DNA; and the enzymes involved in is the synthesis of auxin and encoded by gene 1 and gene 2 of Agrobacterium T-DNA. Yet other examples of male-sterility DNAs encode: glucanases; lipases such as phospholipase $A_2$ (Verheij et al (1981) Rev. Biochem. Pharmacol. 91, 92–203); lipid peroxidases; or plant cell wall inhibitors. Still other examples of male-sterility DNAs encode proteins toxic to plants cells, such as a bacterial toxin (e.g., the B-fragment of diphtheria toxin or botulin).

Still another example of a male-sterility DNA is an antisense DNA which encodes a strand of DNA complementary to a strand of DNA that is naturally transcribed in the plant's stamen cells under the control of an endogenous promoter as described, for example, in European patent publication 0,223,399. Such an antisense DNA can be transcribed into an RNA sequence capable of binding to the coding and/or non-coding portion of an RNA, naturally produced in the stamen cell, so as to inhibit the translation of the naturally produced RNA. An example of such an antisense DNA is the antisense DNA of the TA29 gene (described in Example 2) which is naturally expressed, under the control of the TA29 promoter, in tapetum cells of the anthers of plants.

A further example of a male-sterility DNA encodes a specific RNA enzyme (i.e., a so-called "ribozyme"), capable of highly specific cleavage against a given target sequence, as described by Haseloff and Gerlach (1988) Nature 334, 585–591. Such a ribozyme is, for example, the ribozyme targeted against the RNA encoded by the TA29 gene.

Still other examples of male-sterility DNAs encode products which can render the stamen cells susceptible to specific diseases, such as fungus infections. Such a male-sterility DNA can be used in a plant wherein all other cells, in which the male-sterility DNA is not expressed, are resistant to the specific disease.

By "foreign" with regard to the foreign DNA sequence of this invention is meant that the foreign DNA sequence contains a foreign male-sterility DNA and/or a foreign first promoter. By "foreign" with regard to a DNA, such as a male-sterility DNA and a first promoter, as well a marker DNA, a second promoter and any other DNA in the foreign DNA sequence, is meant that such a DNA is not in the same genomic environment in a plant cell, transformed with such a DNA in accordance with this invention, as is such a DNA when it is naturally found in the cell of the plant, bacteria, animal, fungus, virus, or the like, from which such a DNA originates. This means, for example, that a foreign male-sterility DNA or marker DNA can be: 1) a nuclear DNA in a plant of origin; 2) endogenous to the transformed plant cell (i.e., from a plant of origin with the same genotype as the plant being transformed); and 3) within the same transcriptional unit as its own endogenous promoter and 3' end transcription regulation signals (from the plant of origin) in the foreign DNA sequence of this invention in the transformed plant cell; but 4) inserted in a different place in the nuclear genome of the transformed plant cell than it was in the plant of origin so that it is not surrounded in the transformed plant cell by the genes which surrounded it naturally in the plant of origin. A foreign male-sterility or marker DNA can also, for example, be: 1) a nuclear DNA in a plant of origin; and 2) endogenous to the transformed plant cell; but 3) in the same transcriptional unit as a different (i.e., not its own) endogenous promotor and/or 3' end transcription regulation signals in a foreign chimaeric DNA sequence of this invention in a transformed plant cell. A foreign male-sterility or marker DNA can also, for example, be: 1) a nuclear DNA in a plant of origin; and 2) endogenous to the transformed plant cell; but 3) in the same transcriptional unit as a heterologous promoter and/or 3' end transcription regulation signals in a foreign chimaeric DNA sequence of this invention in a transformed plant cell. A foreign male-sterility or marker DNA can also, for example, be heterologous to the transformed plant cell and in the same transcriptional unit as an endogenous promotor and/or 3' transcription regulation signals (e.g., from the nuclear genome of a plant with the same genotype as the plant being transformed) in a foreign chimaeric DNA sequence of this invention in a transformed plant cell. An example of a foreign male-sterility DNA could come from the nuclear genome of a plant with the same genotype as the plant being transformed and encode a catalytic enzyme, such as a protease or ribonuclease, that is endogenous to stamen cells of the plant being transformed, so that the enzyme is overproduced in transformed stamen cells in order to disturb significantly their metabolism, functioning and/or development. Preferably, the male-sterility DNA and the marker DNA are each heterologous to the plant cell being transformed.

By "heterologous" with regard to a DNA, such as a male-sterility DNA, a first promoter, a marker DNA, a second promoter and any other DNA in the foreign DNA sequence, is meant that such a DNA is not naturally found in the nuclear genome of cells of a plant with the same genotype as the plant being transformed. Examples of heterologous DNAs include chloroplast and mitochondrial DNAs obtained from a plant with the same genotype as the plant being transformed, but preferred examples are chloroplast, mitochondrial, and nuclear DNAs from plants having a different genotype than the plant being transformed, DNAs from animal and bacterial genomes, and chromosomal and plasmidial DNAs from fungal and viral genomes.

By "chimaeric" with regard to the foreign DNA sequence of this invention is meant that at least one of its male-sterility DNAs: 1) is not naturally found under the control of its first promoter for the one male-sterility DNA; and/or 2) is not naturally found in the same genetic locus as at least one of its marker DNAs. Examples of foreign chimaeric DNA sequences of this invention comprise: a male-sterility DNA of bacterial origin under the control of a first promoter of plant origin; and a male-sterility DNA of plant origin under the control of a first promoter of plant origin and in the same genetic locus as a marker DNA of bacterial origin.

So that the male-sterility DNA is expressed selectively in stamen cells of a plant, it is preferred that the first promoter, which controls the male-sterility DNA in the foreign DNA sequence, be a promoter capable of directing gene expression selectively in stamen cells of the plant. (By "stamen" is meant the organ of the flower that produces the male gamete and that includes an anther and a filament). Such a stamen-specific promoter can be an endogenous promoter or an exogenous promoter and can be from the nuclear genome or from the mitochondrial or chloroplast genome of a plant cell. In any event, the first promoter is foreign to the nuclear genome of the plant cell, being transformed. Preferably, the first promoter causes the male-sterility DNA to be expressed only in anther, pollen or filament cells, especially in tapetum or anther epidermal cells. The first promoter can be selected and isolated in a well known manner from the species of plant, to be rendered male-sterile, so that the first promoter directs expression of the male-sterility DNA selectively in stamen cells so as to kill or disable the stamen and render the plant incapable of producing fertile male gametes. The first promoter is preferably also selected and isolated so that it is effective to prevent expression of the male-sterility DNA in other parts of the plant that are not involved in the production of fertile pollen, especially in female organs of the plant. For example, a suitable endogenous stamen-specific first promoter can be identified and isolated in a plant, to be made male-sterile, by:

1. searching for an mRNA which is only present in the plant during the development of its stamen, preferably its anthers, pollen or filament;
2. isolating this stamen-specific mRNA;
3. preparing a cDNA from this stamen-specific mRNA;
4. using this cDNA as a probe to identify the regions in the plant genome which contain DNA coding for the stamen-specific mRNA; and then
5. identifying the portion of the plant genome that is upstream (i.e., 5') from the DNA coding for the stamen-specific mRNA and that contains the promoter of this DNA.

Examples of such first promoters are the TA29 promoter, the TA26 promoter and the TA13 promoter, hereinafter described in the Examples, which have been isolated from tobacco and are tapetum-specific promoters. Another tapetum-specific first promoter from another plant species can be isolated from its genome, using the TA29, TA26 or TA13 gene as a probe as in step 4, above. Under hybridizing conditions, such a probe will hybridize to DNA coding for a tapetum-specific mRNA in a mixture of DNA sequences from the genome of the other plant species (Maniatis et al (1982) *Molecular Cloning. A Laboratory Manual*. Ed. Cold Spring Harbor Laboratory). Thereafter, as in step 5 above, the other tapetum-specific first promoter can be identified.

If more than one male-sterility DNA is present in the foreign DNA sequence of this invention, all the male-sterility DNAs can be under the control of a single first promoter, but preferably, each male-sterility DNA is under the control of its own separate first promoter. Where a plurality of male-sterility DNAs are present in the foreign DNA sequence, the male-sterility DNA also can encode the same or different first RNA(s), polypeptide(s) and protein(s). For example, when the male-sterility DNA encodes an RNase such as RNase T1, it preferred that at least 3, particularly 4 to 6, copies of the male-sterility DNA and its first promoter be provided in the foreign DNA sequence. In any event, all the male-sterility DNA(s) and their first promoter(s) are preferably adjacent to one another in the foreign DNA sequence and in any vector used to transform plant cells with the foreign DNA sequence.

The selection of the marker DNA also is not critical. A suitable marker DNA can be selected and isolated in a well known manner, so that it encodes a second RNA, protein or polypeptide that allows plants, expressing the marker DNA, to be easily distinguished and separated from plants not expressing the second RNA, protein or polypeptide. Examples of marker DNAs encode proteins that can provide a distinguishable color to plant cells, such as the A1 gene encoding dihydroquercetin-4-reductase (Meyer et al (1987) Nature 330, 677–678) and the glucoronidase gene (Jefferson et al (1988) Proc. Natl. Acad. Sci. USA ("PNAS") 83, 8447), or that provide a specific morphological characteristic to the plant such as dwarf growth or a different shape of the leaves. Other examples of marker DNAs confer on plants: stress tolerance, such as is provided by the gene encoding superoxide dismutase as described in European patent application 88/402222.9; disease or pest resistance such as is provided by a gene encoding a *Bacillus thuringiensis* endotoxin conferring insect resistance as described in European patent application 86/300291.1 or a gene encoding a bacterial peptide that confers a bacterial resistance as described in European patent application 88/401673.4

Preferred marker DNAs encode second proteins or polypeptides inhibiting or neutralizing the action of herbicides such as: the sfr gene and the sfrv gene encoding enzymes conferring resistance to glutamine synthetase inhibitors such as Biolaphos and phosphinotricine as described in European patent application 87/400,544.0; genes encoding modified target enzymes for certain herbicides that have a lower affinity for the herbicides than naturally produced endogenous enzymes, such as a modified glutamine synthetase as target for phosphinotricine as described in European patent publication 0,240,792 and a modified 5-enolpyruvylshikimate-3 phosphate synthase as a target for glyphosate as described in European patent publication 0,218,571.

The second promoter, which controls the marker DNA, can also be selected and isolated in a well known manner so that the marker DNA is expressed either selectively in one or more specific tissues or specific cells or constitutively in the entire plant, as desired depending on the nature of the second RNA, protein or polypeptide encoded by the marker DNA. For example, if the marker DNA encodes an herbicide resistance, it may be useful to have the marker DNA expressed in all cells of the plant, using a strong constitutive second promoter such as a 35S promoter (Odell et al (1985) Nature 313, 810–812), a 35S'3 promoter (Hull and Howell (1987) Virology 86, 482–493), the promoter of the nopaline synthetase gene ("PNOS") of the Ti-plasmid (Herrera-Estrella (1983) Nature 303, 209–213) or the promoter of the octopine synthase gene ("POCS" [De Greve et al (1982) J. Mol. Appl. Genet. 1 (6), 499–511]). If the marker DNA encodes a protein conferring disease resistance, it may be useful to have the marker DNA selectively expressed in wound tissue by using, for example, a TR promoter such as the TR1' or TR2' promoter of the Ti-plasmid (Velten et al (1984) EMBO J. 3, 2723–2730). If the marker DNA encodes a herbicide resistance, it may be useful to have the marker DNA selectively expressed in green tissue by using, for example, the promoter of the gene encoding the small subunit of Rubisco (European patent application 87/400, 544.0). If the marker DNA encodes a pigment, it may be useful to have the marker DNA expressed in specific cells, such as petal cells, leaf cells or seed cells, preferably in the outside layer of the seed coat.

One can identify and isolate in a well known manner a tissue-specific second promoter for a plant to be rendered male-sterile and easily distinguishable from non-transformed plants by:

1. searching for an mRNA which is only present in the plant during the development of a certain tissue, such as its petals, leaves or seeds;
2. isolating this tissue-specific mRNA;
3. preparing a cDNA from this tissue-specific mRNA;
4. using this cDNA as a probe to identify the regions in the plant genome which contain DNA coding for the tissue-specific mRNA; and then
5. identifying the portion of the plant genome that is upstream from the DNA coding for the tissue-specific mRNA and that contains the promoter for said DNA.

If more than one marker DNA is present in the foreign DNA sequence of this invention, all the marker DNAs can be under the control of a single second promoter, but preferably, each marker DNA is under the control of its own separate second promoter. More preferably, each marker DNA is under the control of its own second promoter and encodes a different second RNA, protein or polypeptide, providing different distinguishable characteristics to a transformed plant. In any event, the marker DNA(s) and second promoter(s) should be adjacent to each other and to the one or more male-sterility DNAs contained in the foreign DNA sequence of this invention and in any vector used to transform plant cells with the foreign DNA sequence.

It is generally preferred that the first RNA, protein or polypeptide, encoded by the male-sterility DNA, interfere significantly with the stamen cells' metabolism, functioning and/or development by acting in the cytoplasm or the nucleus of the stamen cells. However, when it is desired to have the first protein or polypeptide and/or of the second protein or polypeptide transported from the cytoplasm into chloroplasts or mitochondria of the cells of transformed plants, the foreign DNA sequence can further include an additional foreign DNA encoding a transit peptide. The additional DNA is between the male-sterility DNA and the first promoter if the first protein or polypeptide is to be so-transported and is between the marker DNA and the second promoter if the second protein or polypeptide is to be so-transported. By "transit peptide" is meant a polypeptide fragment which is normally associated with a chloroplast or mitochondrial protein or subunit of the protein and is produced in a cell as a precursor protein encoded by the nuclear DNA of the cell. The transit peptide is responsible for the translocation process of the nuclear-encoded chloroplast or mitochondrial protein or subunit into the chloroplast or the mitochondria, and during such a process, the transit peptide is separated or proteolytically removed from the chloroplast or mitochondrial protein or subunit. One or more of such additional DNA's can be provided in the foreign DNA sequence of this invention for transporting one or more first or second proteins or polypeptides as generally described in European patent applications 85/402,596.2 and 88/402,222.9 and in: Van den Broeck et al (1985) Nature 313, 358–363; Schatz (1987) Eur. J. of Bioch. 165, 1–6; and Boutry et al (1987) Nature 328, 340–342. An example of a suitable transit peptide for transport into chloroplasts is the transit peptide of the small subunit of the enzyme RUBP carboxylase (European patent application 85/402,596.2) and an example of a transit peptide for transport into mitochondria is the transit peptide of the enzyme Mn-superoxide dismutase (see Example 16).

In the foreign DNA sequence of this invention, 3' transcription regulation signals can be selected among those which are capable of enabling correct transcription termination and polyadenylation of mRNA in plant cells. The transcription regulation signals can be the natural ones of the gene to be transcribed but can also be foreign or heterologous. Examples of heterologous transcription regulation signals are those of the octopine synthase gene (Gielen et al (1984) EMBO J. 3, 835–845) and the T-DNA gene 7 (Velten and Schell (1985) Nucleic Acids Research ("NAR") 13, 6981–6998).

Also in accordance with this invention, plant cell cultures, such as anther cell cultures, containing the foreign DNA sequence of this invention in which the first promoter effects expression of the male-sterility DNA at a given stage of pollen development, more especially after meiosis, can be used to regenerate homozygous dominant male-sterile plants ("Efficient isolation of microspores and the production of microspore-derived embryos from *Brassica napus*", E. B. Swanson, M. P. Coumans, S. C. Wu, T. L. Barby and W. D. Beversdorf, Plant Cell Reports (1987) 6: 94–97).

Further in accordance with this invention, processes are provided for producing hybrid seeds which can be grown into hybrid plants. One process involves crossing a nuclear male-sterile plant including at least one marker DNA with a male-fertile plant without the marker DNA. Both male-sterile and male-fertile plants are planted in separate rows near to each other. Another process involves crossing a nuclear male-sterile plant including at least two different marker DNAs with a male-fertile plant including, in common, only one of the two different marker DNAs in a homozygous form. Both male-sterile and male-fertile parent plants can be grown in a substantially random population, increasing the chances of cross-pollination, without the need for precise planting patterns. The male-fertile parent plant can thereafter be easily removed from the population, using the distinctive trait encoded by the non-common marker DNA which is not possessed by the male-fertile parent plant. Preferably in this process, the non-common marker DNA in the male-sterile plant is under the control of a constitutive promoter and encodes a protein or polypeptide that renders the male-sterile plant resistant to a particular herbicide. The male-fertile plant can then be destroyed after cross-pollination, using the particular herbicide.

Plants, transformed with the male-sterility DNA, preferably with both the male-sterility DNA and the marker DNA encoding herbicide-resistance, stably integrated and transmissible throughout generations as dominant alleles in accordance with this invention, are alternatives to, and provide several advantages over, presently used cytoplasmic male-sterility systems for breeding and producing hybrid crops. Such advantages include:

1. For cross-pollinating crops, the breeding strategy is much simplified, because it is not necessary to introduce a restorer gene into the male-fertile parent line of the cross that will produce the commercially sold hybrid seed. Indeed, a heterozygous nuclear male-sterile parent line crossed with another male-fertile parent line for commercial seed production will produce 50% male-sterile hybrid offspring and 50% male-fertile hybrid offspring, as a result of which the commercial crop will produce enough pollen to guarantee full seed set and therefore normal yield. Examples for such crops are corn and oilseed rape.

2. For crops for which the seeds do not represent the economic harvest, the breeding strategy is also much simplified without the need of a restorer gene expressed in the male-fertile parent line. Indeed, for these crops it does not matter that 50% of the commercially sold hybrid seeds are male-sterile. Examples for these crops are sugarbeet and alfalfa.

3. The system allows production of nuclear male-sterile lines and maintainer lines from existing inbred lines in one operation, eliminating the need for backcrossing. This reduces the time lag between conception and commercialization of a hybrid by at least 6 to 8 generations. An example of a typical strategy for producing hybrid plants using as parent plant the plants having inserted and expressing the male-sterility DNA may consist of the following steps:

1) making test hybrids by hand, by crossing inbred lines, and testing for combining ability and selected characteristics (2 years).

2) making one parent line of each of the selected hybrids nuclear male-sterile by the process which is the object of this invention (1 year).

3) multiplying the nuclear male sterile parent plant obtained from said process, hereinafter called "$A^S$", and its maintainer line, hereinafter called "A", and the pollinating male-fertile parent plant, hereinafter called "B", of the future commercial crop (3 years). During the same period, introducing the selected hybrids in official yield trials (3 years).

4) producing and selling the approved hybrid seed (1 year).

4. Combined with a marker DNA encoding herbicide-resistance, such a nuclear male-sterility system allows production of 2-, 3- and 4-way hybrids in any combination required. It is believed to be sufficient to introduce the male-sterility DNA and adjacent thereto the marker DNA into the nuclear genome of one plant which will be used as one of the grandparent breeding lines for obtaining 2- or 3-way hybrids, and into the nuclear genome of two plants which will be used as the two grandparent lines for 4-way hybrids. Each breeding line can be maintained by the following two crosses given here by way of example, and whereby "SH" stands for the dominant alleles respectively of male-sterility (S) and herbicide resistance (H), and sh stands for the recessive alleles respectively of male fertility (s) and herbicide sensitivity (h):

a. SH/sh x sh/sh gives 50% SH and 50% sh offspring, and after spraying with the herbicide to which H confers resistance, 100% sterile seedlings are obtained.

b. sh/sh x sh/sh gives 100% fertile offspring.

5. It provides a protection for the owner of the marker DNA that has been integrated into the male-sterility system by making it more difficult for competitors to breed the marker DNA into their own breeding lines.

For illustrative purposes, two crop breeding schemes in accordance with this invention are given as follows:

Scheme 1: Breeding a Plant Containing Adjacent Male-sterility DNA and Marker DNA Encoding Herbicide-resistance 1A) Maintaining the Male-sterility Line $A^S$:

line $A^{SH/sh}$ x line $A^{sh/sh}$ giving 50% $A^{SH/sh}$ (phenotype: male-sterile, herbicide-resistant) 50% $A^{sh/sh}$ (phenotype: male-fertile, herbicide-susceptible)

1B) Producing the Hybrid Seed Crop:

a) planting seeds of $B^{sh/sh}$ (male plants) and the seeds obtained by the cross 1A) consisting of $A^{SH/sh}$ and $A^{sh/sh}$ ("female" plants) in separate rows.

b) eliminating the genotype $A^{sh/sh}$ by spraying the female rows with the herbicide.

c) cross-pollination occurring: $A^{SH/sh}$ x $B^{sh/sh}$ and $B^{sh/sh}$ x $B^{sh/sh}$ giving in the female rows: 50% $AB^{SH/sh}$ (phenotype: hybrid, male-sterile, herbicide-resistant) 50% $AB^{sh/sh}$ (phenotype: hybrid, male-fertile, herbicide-sensitive) and in the male rows: 100% $B^{sh/sh}$.

d) eliminating the genotype $B^{sh/sh}$ occurring in the male rows by spraying with the herbicide or by mechanical means.

e) harvesting the hybrid seeds of the female rows wherein the cross-pollination of c) occurred This is the commercially sold seed.

Scheme 2: Breeding a Plant Containing Adjacent Male-sterility DNA and Two Marker DNAs. Each Encoding a Different Herbicide-resistance (H1 and H2)

2A) Maintaining the Male-sterile Line $A^S$:

$A^S$:$A^{SH1H2/sh1h2}$ × $A^{sh1h2/sh1h2}$ giving 50% $A^{SH1H2/sh1h2}$ (phenotype: male-sterile, resistant to both herbicides). 50% $A^{sh1h2/sh1h2}$ (phenotype: male-fertile, susceptible to both herbicides).

2B) Maintaining Pollination Line B:

$B^{sh1H2/sh1H2}$ × $B^{sh1H2/sh1H2}$ giving 100% $B^{sh1H2/sh1H2}$ (phenotype: male-fertile, susceptible to herbicide 1 and resistant to herbicide 2).

2C) Producing the Hybrid Seed Crop:
  a) planting the seeds obtained from 2A) and the seeds obtained from 2B) at random.
  b) eliminating the genotype $A^{sh1h2/sh1h2}$ by spraying the field with herbicide 2.
  c) cross-pollination occurring:
  $A^{SH1H2/sh1h2}$ × $B^{sh1H2/sh1H2}$ giving 50% $AB^{SH1H2/sh1H2}$ 50% $AB^{sh1h2/sh1H2}$ and self-pollination occurring: $B^{sh1H2/sh1H2}$ × $B^{sh1H2/sh1H2}$ giving 100% $B^{sh1H2/sh1H2}$
  d) eliminating plants with genotype $B^{sh1H2/sh1H2}$ obtained from the parent line B, for which self-pollination occurred, by spraying the field with herbicide 1.
  e) harvesting hybrid seeds of the remaining plants $A^{SH1H2/sh1H2}$ obtained by the cross-pollination of c).

The following Examples illustrate the invention. The figures referred to in the Examples are as follows:

BRIEF DESCRIPTION OF THE DRAWINGS

FIG. 3A shows the DNA sequence and amino acid sequence of the TA29 gene, from its ClaI site to its Hind III site. Above the sequences, the important restriction sites are indicated, and under the sequences is the amino acid sequence encoded by the ORF. Also indicated are:
  from nucleotide ("nt") 1446 to 1452: TATA box (asterisks),
  at nt 1477: transcription initiation site of TA29 mRNA (asterisk),
  from nt 1514 to 1537: the 3' to 5' sequence of a synthetic oligomer as described in Example 2, and
  from nt 1940 to 2296 (between arrows); the aligned sequence of TA29 cDNA.

FIG. 3B shows the alignment of the TA13 cDNA (top line) and the TA29 cDNA (bottom line); as discussed in Example 4. Homologous nucleotides are indicated by vertical lines.

FIG. 3C shows the sequence of the TA26 cDNA, as discussed in Example 4; the ORF is underlined.

FIG. 7B shows a map of the vector PTTM6A⁻ of Example 11.

FIG. 9B shows a map of the vector pTVEP2 of Example 14.

FIG. 10A shows a map of the vector pTVEP63 of Example 16.

FIG. 10B shows a map of the vector pTVEP62 of Example 16.

Unless otherwise stated in the Examples, all procedures for making and manipulating recombinant DNA were carried out by the standardized procedures described in Maniatis et al, *Molecular Cloning—A Laboratory Manual*, Cold Spring Harbor Laboratory (1982). The following plasmids and vectors, used in the Examples, have been deposited in the Deutsche Sammlung Für Mikroorganismen und Zellculturen ("DSM"), Mascheroder Weg 1B, D-3300 Braunschweig, Federal Republic of Germany under the provisions of the Budapest Treaty:

| Plasmid or vector | DSM Accession No. | Date |
| --- | --- | --- |
| pMB3 | 4470 | 21 Mar. 1988 |
| pGSC1600 | 4467 | 21 Mar. 1988 |
| pGCC1700 | 4469 | 21 Mar. 1988 |
| pGV2260 | 2799 | December 1983 |
| pGSC1701A | 4286 | 22 Oct. 1987 |
| pTTM4 | 4471 | 21 Mar. 1988 |
| pMAC5-8 | 4566 | 25 Apr. 1988 |
| pTTM6 | 4468 | 21 Mar. 1988 |

EXAMPLE 1

Subcloning of an Anther-specific Gene (The "TA29 gene")

Figure 1:
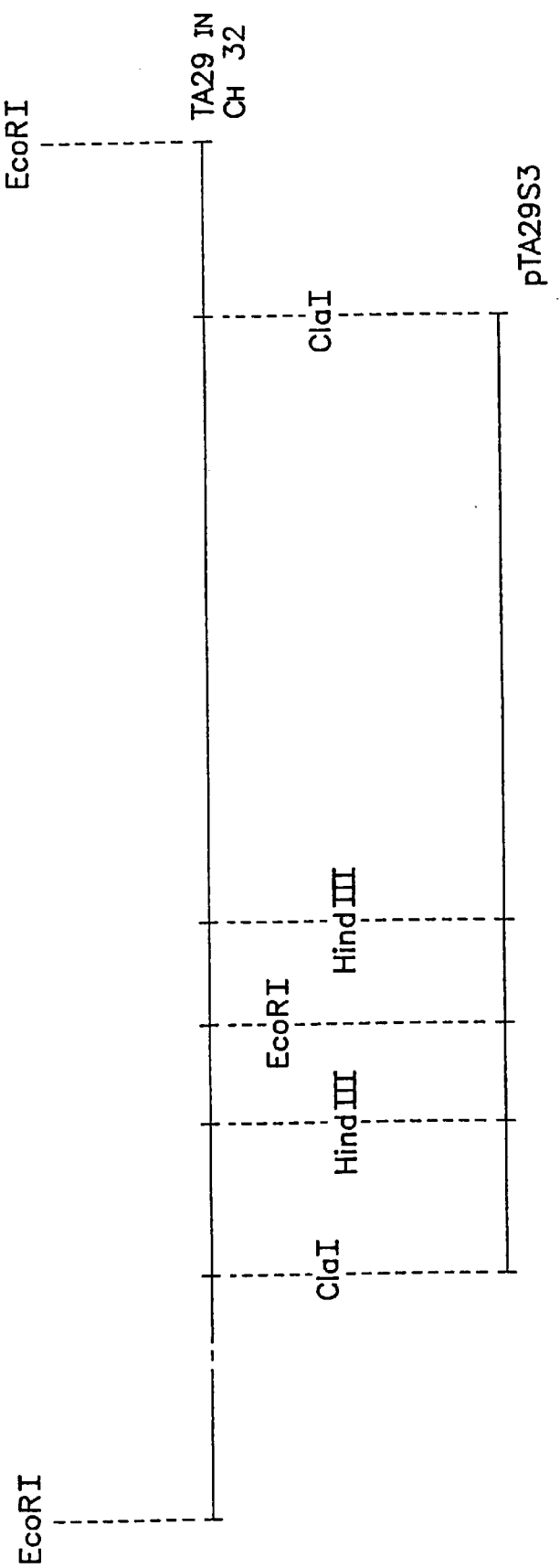
FIG. 1 shows restriction maps of TA29 cDNA and its ClaI fragment in pTA29S3 of Example 1.

From Professor Robert Goldberg of the University of California, Los Angeles (UCLA) were obtained: a *Nicotiana tabacum* anther-specific cDNA ("TA29 cDNA") cloned as a PstI fragment in pBR329 (Covarrubias and Bolivar (1982) Gene 17, 79) by GC tailing; and the corresponding genomic clone ("lambda TA29") that was isolated from a *N. tabacum* "Samsun" genomic library using TA29 cDNA as a probe and that was inserted in the EcoRI site of the lambda phage vector cH32 (Loenen and Blattner (1983) Gene 26, 171). The TA29 cDNA was 365 base pairs long (±0.4 kb) and hybridized to a tapetum-specific mRNA of 1,100 nucleotides which accounts for 0.24% of the poly A⁺ mRNA from anthers of the *N. tabacum*. As shown in FIG. 1, lambda TA29 contains two EcoRI fragments, the total insert measuring 13.2 kb.

An internal 7.5 kb ClaI fragment as shown in FIG. 1, containing the TA29 gene, was subcloned from lambda TA29 in pLK31 (Botterman and Zabeau (1987) DNA 6, 6) which produced a plasmid named "pTA29S3". Nitrocellulose bound fragments of lambda TA29, digested with the combination of EcoRI/ClaI/HindIII/HindIII-EcoRI and the combination of ClaI-EcoRI and hybridized against TA29 cDNA, indicated the presence of sequences homologous to TA29 cDNA.

EXAMPLE 2

Figures 2, 4A:
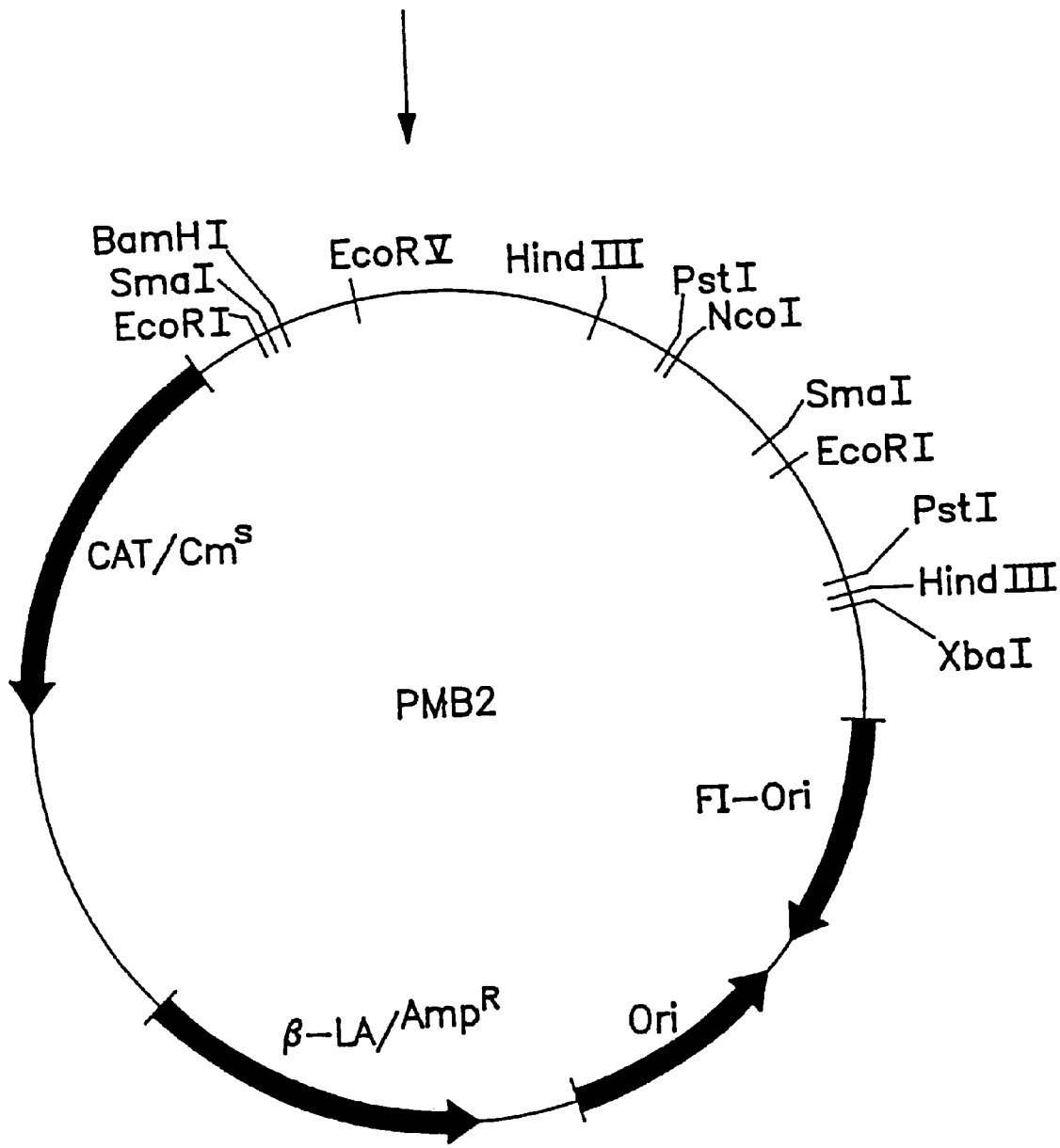
FIG. 2 shows the cDNA sequence of the PstI fragment of the TA29 gene of Example 2.
FIG. 4A shows schematically the construction of the vector pMB2 of Example 3.

Nucleotide Sequence Determination of TA29 cDNA and its Homologous Sequence from pTA29S3; Mapping of TA29 Gene and its Promoter The PstI insert of TA29 cDNA in pBR329 was completely sequenced (Maxam and Gilbert (1977) Proc. Natl. Acad. Sci. USA ("PNAS") 74, 560). The cDNA sequence is shown in FIG. 2. It reveals the presence of one open reading frame over the entire cDNA sequence (as indicated).

Then, the sequence of the ClaI insert in pTA29S3 was determined from the ClaI site to the HindIII site (3261 base pairs apart). Comparison of the TA29 cDNA sequence and the pTA29S3 sequence revealed the presence of a sequence in the pTA29S3 which was completely homologous with the TA29 cDNA sequence.

FIG. 3 shows the sequence of the TA29 gene in pTA29S3. The sequence in pTA29S3 that is identical to the TA29 cDNA sequence is between the arrows in FIG. 3. A putative open reading frame is revealed by the corresponding amino acid sequence in FIG. 3. This indicates that the TA29 gene encodes a protein of 321 amino acid residues and that there are no introns present in the coding region. The length of the open reading frame of 964 (+ leader) nucleotides matches the size of a transcript present in tobacco anther mRNA prepared from anthers isolated from young (12–20 mm long) tobacco flower buds and absent in the mRNA isolated from leaf and older flowers (when the buds are opened and petals have appeared). The size of this mRNA is approximately 1100 nucleotides.

There are two ATG codons, one at nucleotide ("nt") 1527 and the other at nt 1560, which could serve as initiation codon for the open reading frame, 33 nucleotides apart. There is a consensus sequence TATA at nt 1446 present 81 nucleotides 5' upstream of the first ATG codon (indicated by asterisks in FIG. 3). To confirm that this "TATA" box is part of the promoter of the TA29 gene, the 5' end of the TA29 mRNA was determined. This was done by primer extension (Mc Knight et al (1981) Cell 25, 385). For this purpose, an oligomer of 24 nucleotides, having the sequence: 5' GGA GCT ACC ATT TTA GCT AAT TTC 3', was used as it is complementary to the TA29 gene from nt 1514 to nt 1537 as shown in FIG. 3.

This oligonucleotide was $^{32}P$ labeled by kination at the 5' end. After being hybridized with anther mRNA, the oligonucleotide was extended by reverse transcriptase. The resulting extended oligonucleotide was analyzed on a sequencing gel, next to a sequencing ladder, to determine its exact size. The fragment was shown to be 61 nucleotides long. This indicates that transcription initiation of the TA29 mRNA occurred at nt 1477 (indicated by asterisk in FIG. 3). Hence, the TA29 gene has a TATA box located 31 nucleotides upstream of the transcription initiation site. The mRNA contains a 51 nucleotide-long leader sequence from nt 1477 to nt 1527, a coding region of 964 nucleotides from nt 1527 to nt 2491, and a 3' non coding region of approximately 100 nucleotides from nt 2492 to nt 2590. As is the case in approximately 92% of presently characterized plant genes (Joshin (1987) Nucleic Acids Research ("NAR") 15 (16), 6643), it is believed that the first AUG codon of the mRNA is used to initiate translation. The TA29 promoter thus appears to be located between the ClaI restriction site and nt 1477.

EXAMPLE 3

Construction of a Promoter Cassette ("PTA29") Derived from the TA29 Gene

Figure 4B:
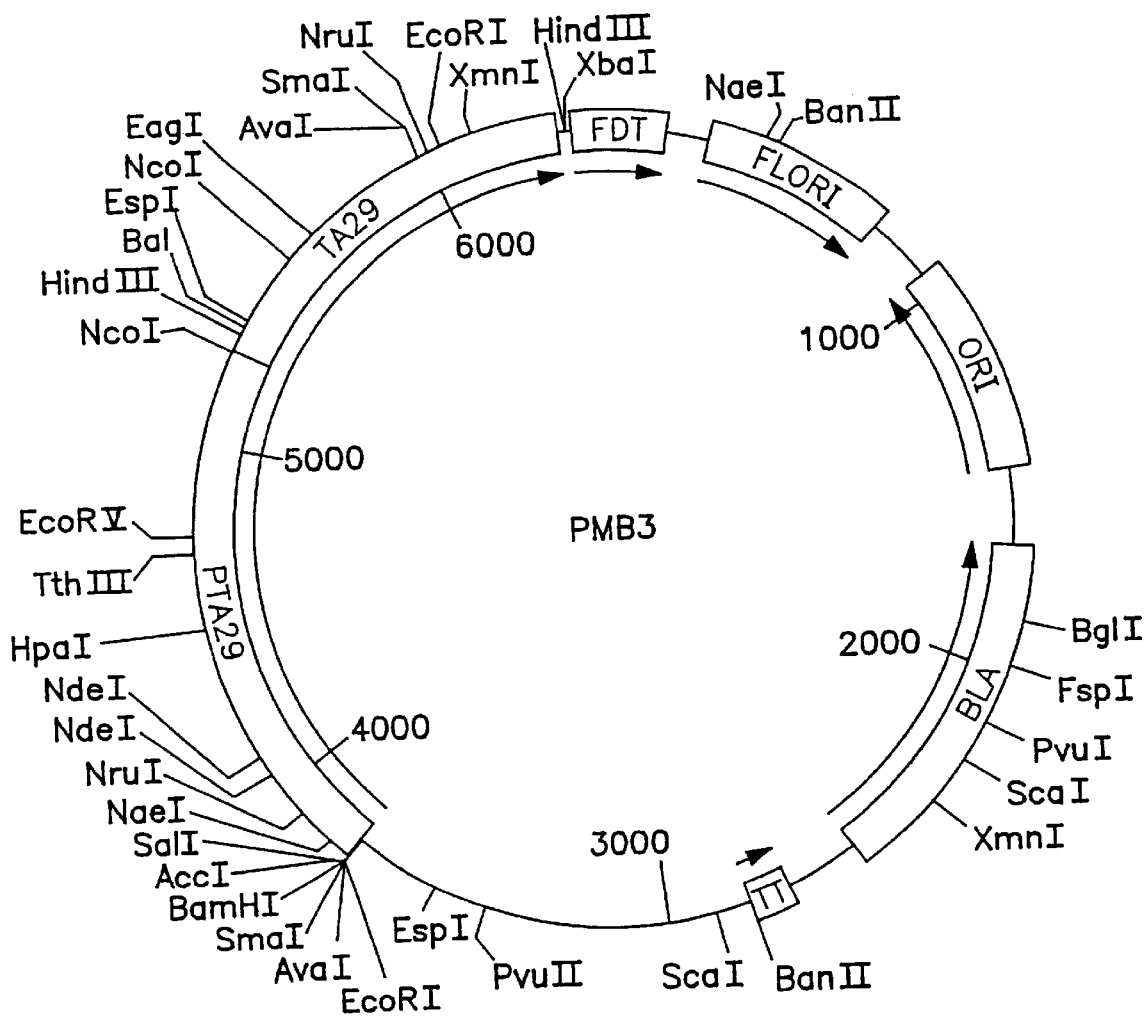
FIG. 4B shows a map of the vector pMB3 of Example 3.

To construct chimaeric DNA sequences containing the 5' regulatory sequences, including the promoter, of the TA29 gene in the same transcriptional unit as, and controlling, a first heterologous male-sterility DNA, a cassette was constructed as shown in FIG. 4 by subcloning a 2.5 kb ClaI/AccI fragment from pTA29S3 into the polylinker AccI site of pMAC 5–8 (European patent application 87/402348.4). This produced a vector named "pMB2", shown in FIG. 4, which could be used to isolate single strand DNA for use in site directed mutagenesis.

Then, the sequence surrounding the first ATG codon AAA ATGGTA was modified to ACC<u>ATG</u>GTA by substituting two adenine residues for cytosine residues. This mutation created the sequence CCATGG which is the recognition site for the restriction enzyme NcoI. This site directed mutagenesis in pMB2 was performed using a synthetic oligonucleotide of 24 nucleotides with the following sequence:

3'GTT TAA TCG ATG GTA CCA TCG AGG 5'

The resulting plasmid, containing the newly created NcoI site, was named "pMB3" and is shown in FIG. 4 bis. The precise nucleotide sequence spanning the NcoI site was determined in order to confirm that it only differed from the 5' sequence of the TA29 gene by the AA—CC substitution, creating the NcoI site. The 1507 nucleotide long fragment ClaI—NcoI was named "PTA29".

EXAMPLE 4

Identification of cDNA Clones Obtained from other Stamen-specific mRNAs

To demonstrate that other anther-specific mRNAs could be identified and then used to isolate cDNA clones with analogous properties to the TA29 gene, two other *N. tabacum* anther-specific cDNAs ("TA13 cDNA" and "TA26 cDNA") were obtained from Professor Goldberg of UCLA.

TA13 cDNA is a clone of 1100 bp which hybridized to two mRNA species of about 1100 and 1200 nucleotides, respectively, which are specific for tapetum cells and are abundant at a very early stage of anther development. TA13 cDNA was sequenced, using the procedure of Example 2, and then compared with the sequence of TA29 cDNA as shown in FIG. 3B. This sequence comparison reveals that TA13 cDNA and TA29 cDNA share 92% homology, and the ORF is very rich in glycine content.

TA26 cDNA was cloned as a PstI insert into pBR329 by poly-G/C tailing. It is a clone of 519 bp which hybridized to one tobacco mRNA species of 580 nucleotides, which mRNA is specific for tapetum cells and abundant at a certain stage of anther development. The entire TA26 cDNA was sequenced using the procedure of Example 2, and when compared with the sequence of TA29 cDNA, revealed no homology. The sequence of TA26 cDNA is given in FIG. 3C.

EXAMPLE 5

Construction of a Chimaeric DNA Sequence of PTA29 and a Glucuronidase Gene

Figure 5:
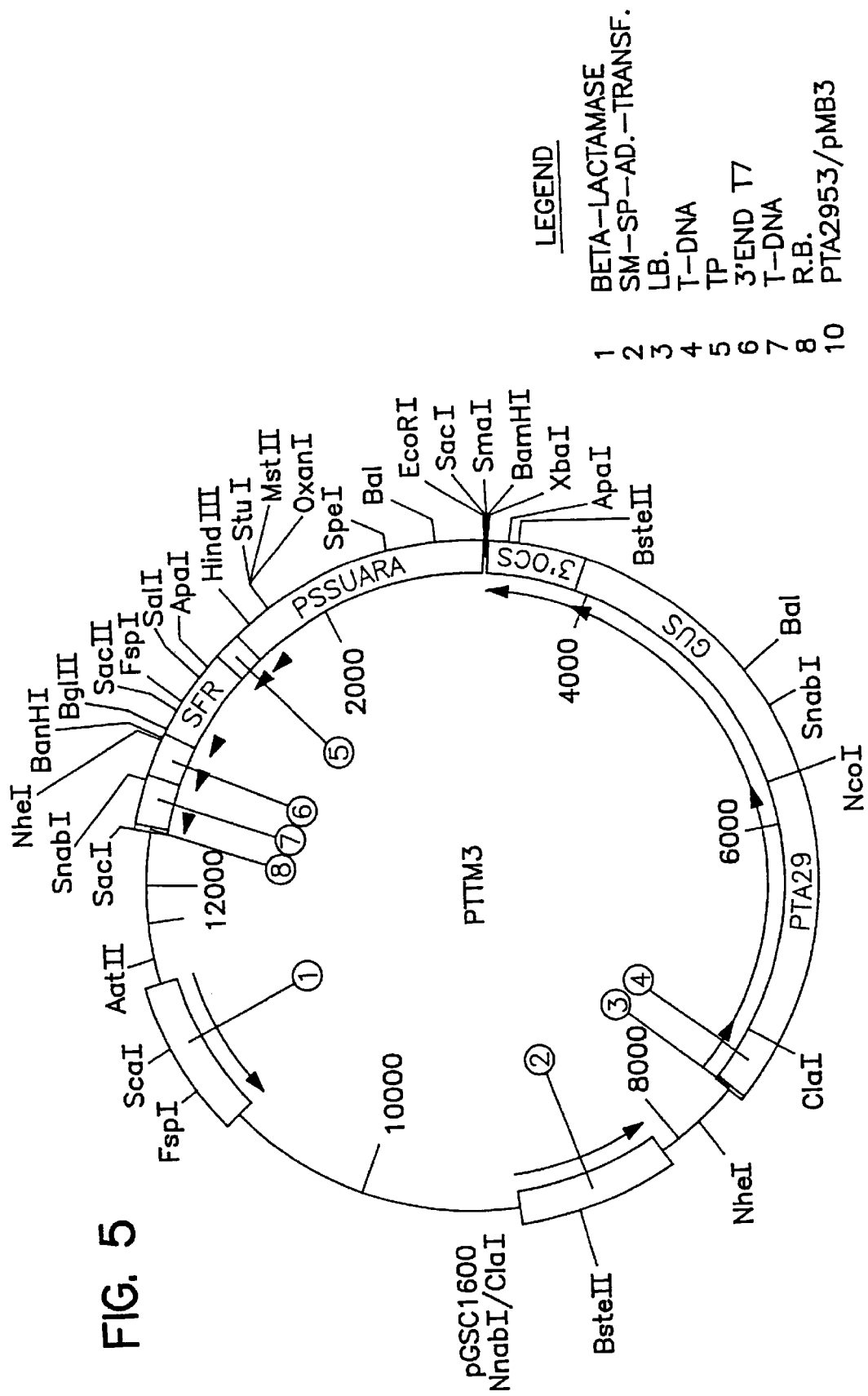
FIG. 5 shows a map of the vector pTTM3 of Example 5.

A plasmid named "pTTM3", shown in FIG. 5, was constructed by assembling the following well known DNA fragments:

1. a vector fragment, including T-DNA border sequences, derived from pGSC1600;
2. a chimaeric sequence containing the promoter cassette PTA29 from Example 3, fused in frame with a pMB3 NcoI/EcoRI fragment containing an *E. coli* gene encoding beta-glucuronidase ("GUS" [Jefferson et al (1986)

PNAS 83, 8447; Jefferson et al (1987) EMBO J. 6, 3901]) and the 3' end signals of an octopine-synthase gene ("OCS" [Dhaese et al (1983) EMBO J. 2, 419]);

3. a chimaeric sequence containing an Arabidopsis SSU promotor ("PSSU" or "PSSUARA"), a herbicide resistance gene sfr (European patent application 87/400,544.0) and the 3' end signals of a T-DNA gene 7 (Velten and Schell (1985) NAR 13, 6981); and 4. a chimaeric sequence containing the EcoRI/SacI fragment from pGSFR401 which contains a nopaline-synthase promotor ("PNOS"), a neo gene encoding kanamycin resistance and the 3' end signals of an octopine synthase gene (European patent application 87/400,544.0, wherein pGSFR401 is called "pGSR4").

pTTM3 is a T-DNA vector containing, within the T-DNA border sequences, two chimaeric sequences: PSSU-sfr in which the sfr is a marker DNA (European patent application 87/400,544.0) under the control of PSSU as a second promoter; and PTA29-GUS in which GUS is a reporter gene whose expression in plants and plant cells under the control of the TA29 promoter can easily be localized and quantified.

EXAMPLE 6

Introduction of the Chimaeric DNA Sequence of Example 5 into Tobacco

A recombinant Agrobacterium strain was constructed by mobilizing pTTM3 (from Example 5) from *E. coli* into Agrobacterium C58C1 Rif$^R$ containing pGV2260 (De Blaere et al (1985) NAR 13, 4777). Mobilization was carried out using *E. coli* HB101 containing pRK2013 (Figurski et al (1979) PNAS 76, 1648) as a helper as described in European patent publication 0,116,718. The resulting Agrobacterium strain contained a hybrid Ti-plasmid comprising pGV2260 and pTTM3.

This strain was used to transform tobacco leaf discs (*N. tabacum* Petite Havane SR1) using standard procedures as described, for example, in European patent application 87/400,544.0. Transformed calli and shoots were selected using 5 mg/l of the herbicide phosphinothricin in the medium (De Block et al (1987) EMBO J. 6, 2513). No beta-glucuronidase enzyme activity was detected in the transformed herbicide-resistant calli and shoots.

Then, the transformed shoots were rooted, transferred to soil in the greenhouse and grown until they flowered. The flowers were examined, and only the tapetum cells in the anthers of the stamen were found to contain beta-glucuronidase activity. This shows that the TA29 promoter is capable of directing expression of a heterologous gene, like the beta-glucuronidase gene, selectively in tapetum cells of the plants.

EXAMPLE 7

Construction of a Chimaeric DNA Sequence of PTA29 and a Gene 4

Figure 6:
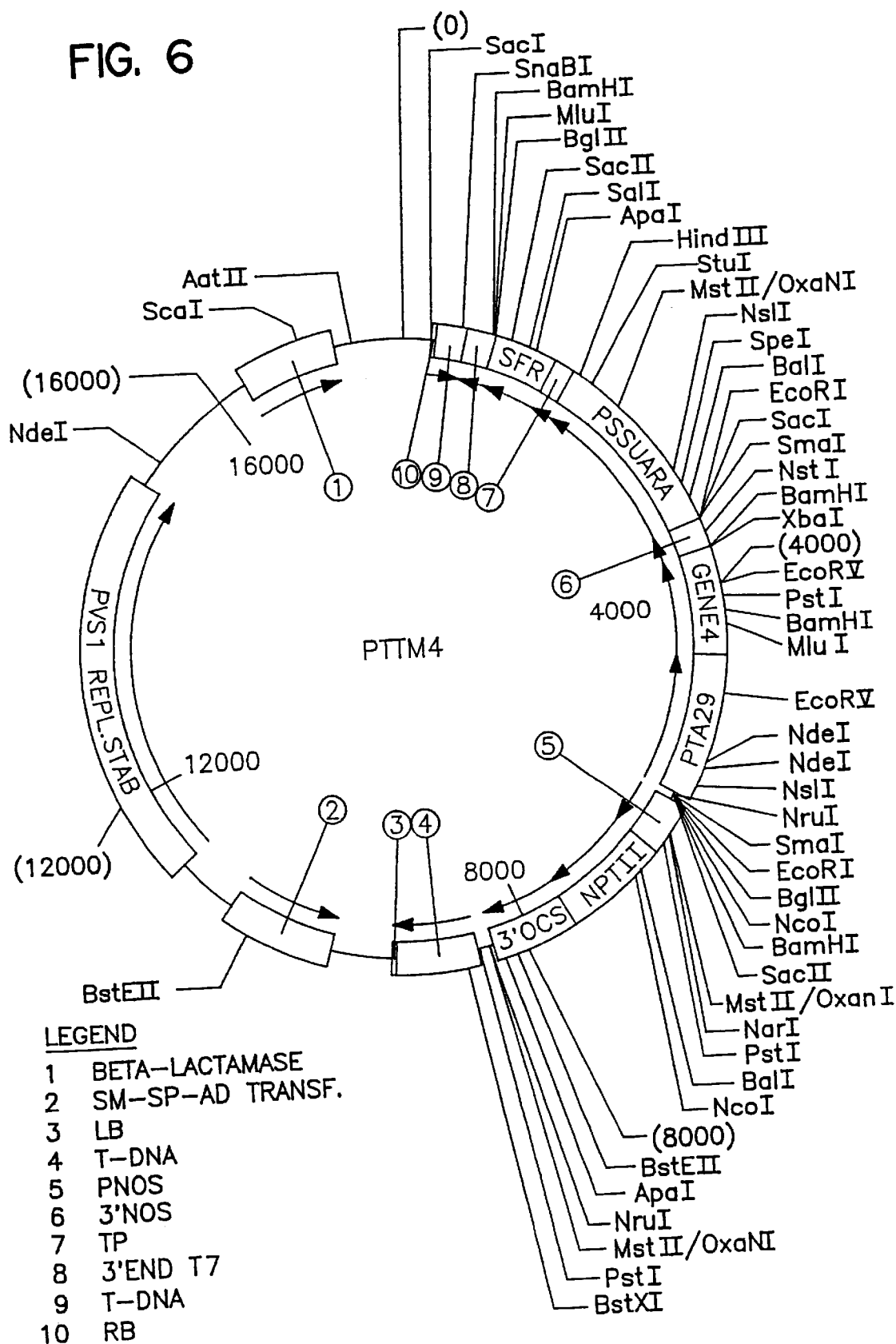
FIG. 6 shows a map of the vector pTTM4 of Example 7.

A plasmid named "pTTM4", shown in FIG. 6, was constructed by assembling the following well known DNA fragments:

1. a vector fragment, including T-DNA border sequences, derived from pGSC1700 (Cornellisen and Vandewiele (1989) NAR 17 (1), 19–29);
2. the chimaeric sequence (no. 3) of Example 5, containing the PSSU promotor controlling expression of herbicide-resistance gene sfr and the 3' end of a T-DNA gene 7;
3. the chimaeric sequence (no. 4) of Example 5, containing the PNOS promoter controlling expression of the neo gene and the 3' end of the octopine synthase gene; and
4. a chimaeric sequence containing the PTA29 promotor cassette from Example 3, fused in frame with an Acrobacterium T-DNA gene 4 that encodes isopentenyl transferase (Akiyoshi et al (1984) PNAS 76, 5994; Barry et al (1984) PNAS 81, 4776) containing its own 3' end transcription regulation signals.

pTTM4 is a binary type T-DNA vector containing, within the T-DNA border sequences, the following chimaeric sequences: PSSU-sfr and PNOS-neo in which the sfr and neo genes are marker DNAs that encode dominant selectable markers for plants and that are under the control of respectively PSSU and PNOS as second promoters; and PTA29-gene 4 in which gene 4 is a male-sterility DNA that is under the control of PTA29 as a first promoter and encodes the enzyme isopentenyl transferase which will cause the enhanced production of cytokinin. Enhanced cytokinin production in tapetum cells, under the control of the TA29 promoter, will disturb the metabolism and organogenesis of the tapetum cells.

EXAMPLE 8

Introduction of the Chimaeric DNA Sequence of Example 7 into Tobacco

As described in Example 6, pTMM4 (from Example 7) was introduced with mobilization from *E. coli* into Agrobacterium C58C1 Rif$^R$. The resulting Agrobacterium strain contained a binary type Ti-plasmid comprising pGV2260 and pTTM4.

As also described in Example 6, this strain was used to transform tobacco leaf discs, and transformed calli and shoots were selected using 5 mg/l of phosphinothricin. Transformed herbicide-resistant shoots were rooted, which shows that gene 4 was not yet being expressed in the transformed plants.

The plants were then transferred to soil in the greenhouse and grown until they flower. The flowers are examined, and no functional tapetum cells are found in their anthers of their stamen. This shows that the TA29 promoter is capable of directing expression of the heterologous gene 4 selectively in tapetum cells of the plants.

EXAMPLE 9

Construction of a Chimaeric DNA Sequence of PTA29 and a RNAse T1 Gene

Figure 7A:
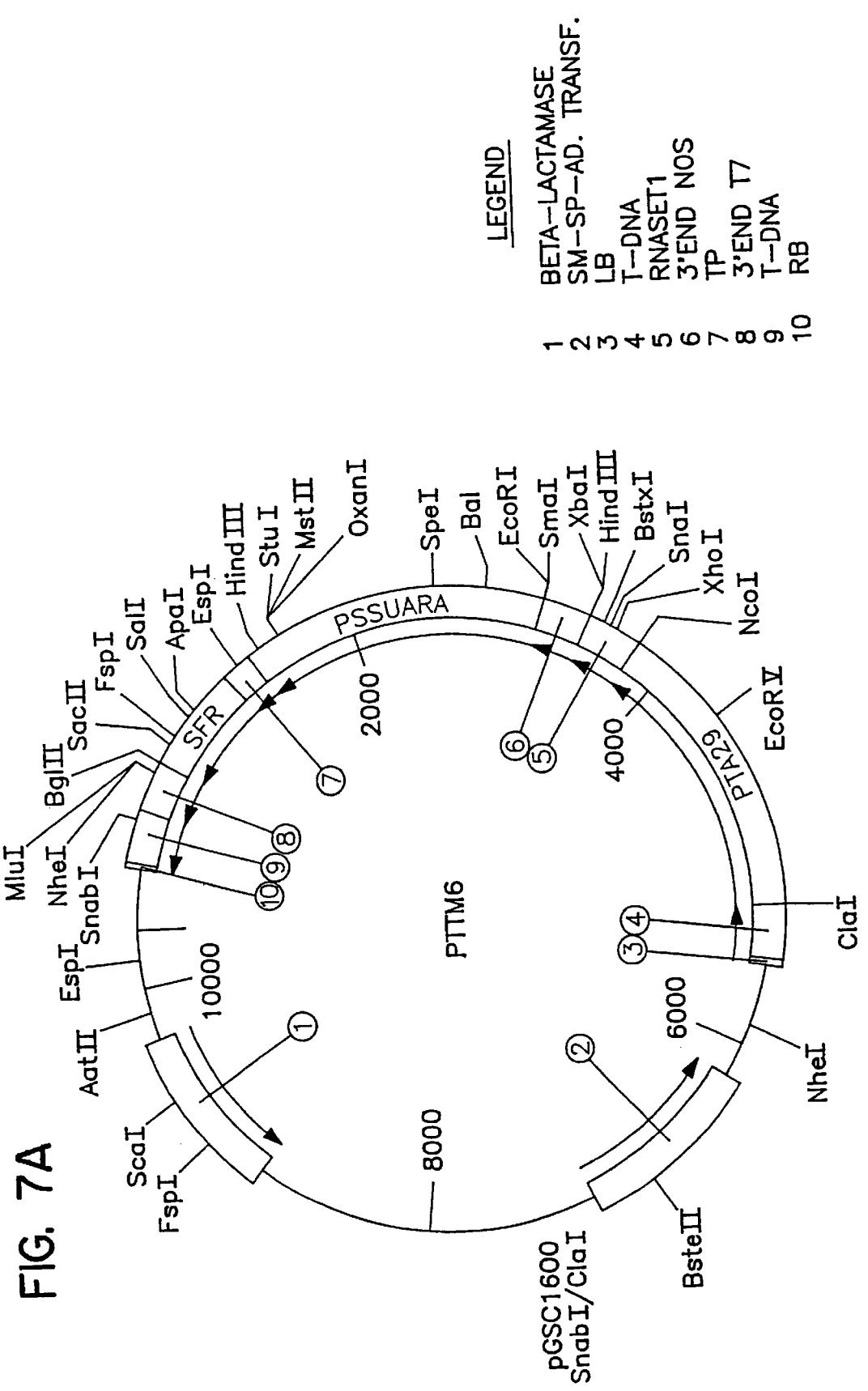
FIG. 7A shows a map of the vector pTTM6 of Example 9.

A plasmid named "pTTM6", shown in FIG. 7A, was constructed by assembling the following well known DNA fragments:

1. a vector fragment, including T-DNA border sequences, from pGSC1600;
2. the chimaeric sequence (no. 3) of Example 5, containing the PSSU promotor, the herbicide resistance gene sfr and the 3' end of the T-DNA gene 7; and
3. a chimaeric sequence, containing the pTA29 promoter cassette from Example 3, fused in frame with a synthetic gene encoding RNase T1 from *A. orhyzae*, (Quaas et al, "Biophosphates and their Analoques-Synthese, Structure, Metabolism and Activity" (1987) Elsevier Science Publisher B.V., Amsterdam; Quaas et al (1988) Eur. J. Biochem. 173, 617–622.) and the 3' end signals of a nopaline synthase ("NOS") gene (An et al (1985) EMBO J. 4 (2), 277).

pTTM6 is a T-DNA vector containing, within the T-DNA border sequences, two chimaeric sequences; PSSU-sfr which is a marker DNA under the control of PSSU as a second promoter; and PTA29-RNase T1 gene which is a male-sterility DNA under the control of PTA29 as a first promoter. Expression in tapetum cells of the male-sterility DNA under the control of the TA29 promoter will produce RNase T1 that will be lethal for the cells, since the RNase T1 will degrade the RNA molecules which are indispensable for these cells' metabolism.

EXAMPLE 10

Introduction of the Chimaeric DNA Sequence of Example 9 into Tobacco

As described in Example 6, a recombinant Agrobacterium strain was constructed by mobilization of pTTM6 (from Example 9) from *E. coli* into Agrobacterium C58C1 Rif$^R$. The resulting Agrobacterium strain, harboring a cointegrated Ti-plasmid comprised of pGV2260 and pTTM6, was used for transforming tobacco leaf discs. Transformed calli and shoots were selected using 5 mg/l phosphinothricin. That the RNase T1 gene was not expressed in the transformed herbicide-resistant calli and shoots was shown by their growth.

Figure 11A:
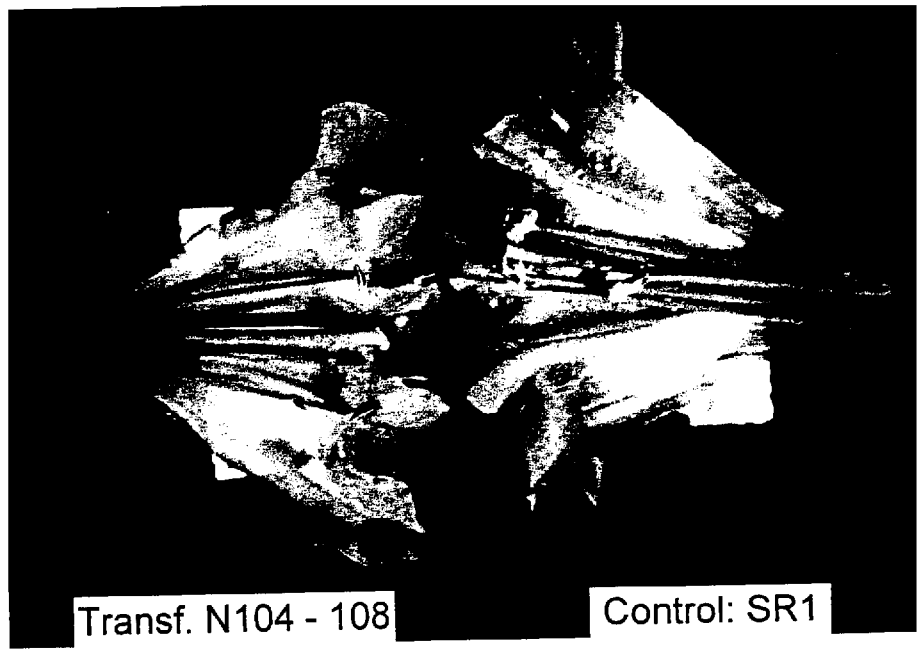
FIG. 11 shows a photograph of flowers of normal tobacco plants compared with flowers of tobacco plants transformed with the male-sterility DNA of Example 9.
Figure 11B:
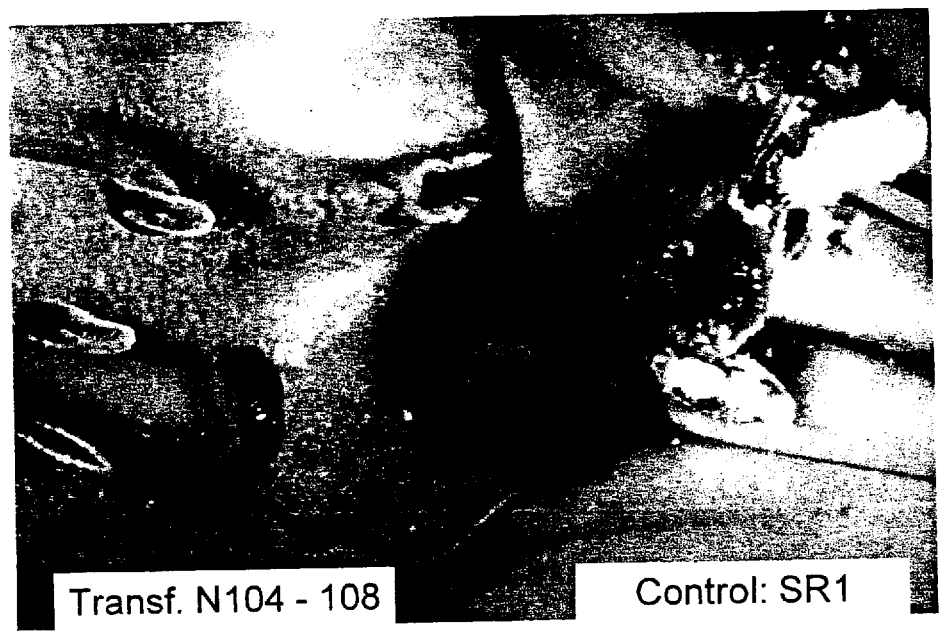

The transformed shoots were rooted, transferred to soil in the greenhouse and grown until they flowered. The transformed tobacco plants developed normal flowers except for their anthers. The anthers, although of normal shape, dehisched later in time, compared to the anthers of non-transformed tobacco plants (see FIG. 11). Upon dehiscense, either little or no pollen was released from the transformed plants, and the pollen grains formed by the transformed plants, were about 50 to 100 times smaller in volume than normal pollen grains and were irregularly shaped. Moreover, most of the pollen grains from transformed plants failed to germinate, and the germination efficiency of pollen from transformed plants was about 0 to 2% of the germination efficiency of normal pollen grains. Furthermore, the transformed plants did not produce any seeds by self-pollination—neither by natural self-pollination nor by hand-provoked self-pollination.

Figure 12A:
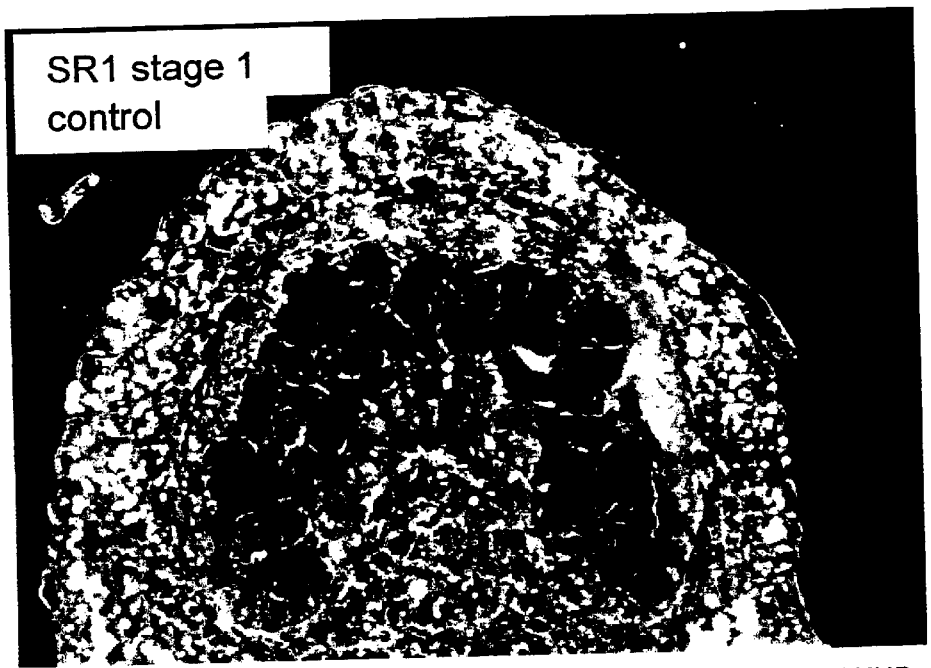
FIG. 12 shows a photograph of a transverse cutting of the anther of a normal tobacco plant compared with the anther of a tobacco plant transformed with the male-sterility DNA of Example 9 (enhancement: ×250).
Figure 12B:
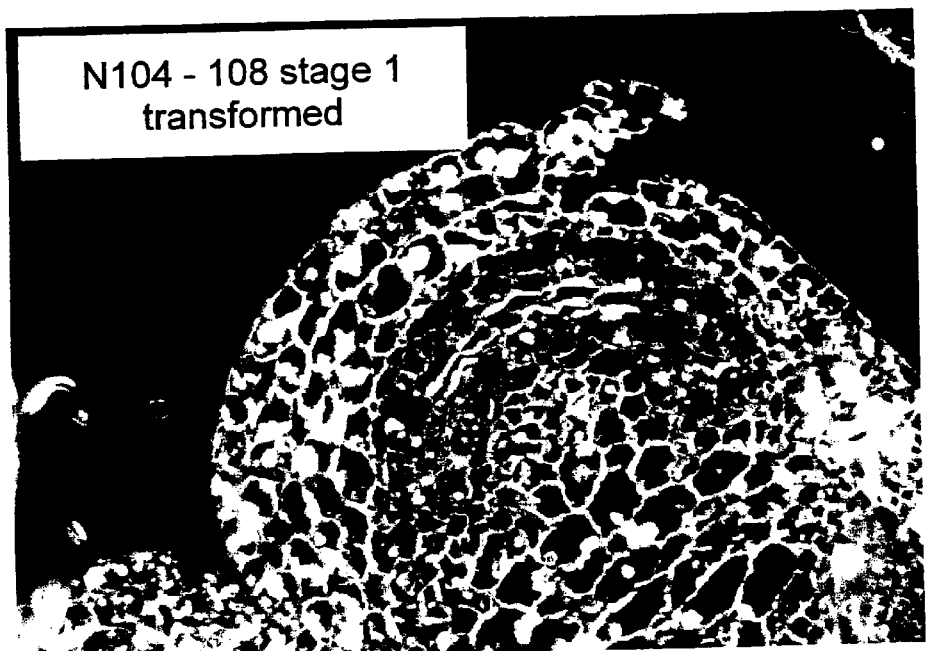

Microscopic evaluation, by thin layer cross section, of a transformed plant showed that no normal tapetum layer was formed and that the pollen sack remained empty (see FIG. 12 ). This shows that the TA29 promoter is capable of directing expression of the heterologous RNase T1 gene selectively in tapetum cells of the transformed plants, and that the RNase T1 is capable of sufficiently disturbing the functioning of the tapetum cells, so as to render the plants male-sterile.

EXAMPLE 11

Introduction of a Derivative of the Chimaeric DNA Sequence of Example 9 into Oilseed Rape A recombinant Agrobacterium strain was constructed by mobilization of pTTM6A⁻ from *E. coli* into Agrobacterium C58 Rif$^R$ containing pMP90 (Koncz and Schell (1986) Mol. Gen. Genetics 204, 383–396). pMP90 provides vir and trans functions and does not carry a gene encoding ampicillin resistance. As shown in FIG. 7B, pTTM6A⁻ is a derivative of PTTM6 (from Example 9), in which the β-lactamase gene encoding ampicillin resistance has been inactivated by insertion of a DNA sequence into the ScaI site of the β-lactamase gene.

The resulting Agrobacterium strain (named "A3144"), harboring pMP90 and pTTM6A⁻, was used for the transformation of *Brassica napus* according to the procedure of Lloyd et al (1986) Science 234, 464–466 and Klimaszewska et al (1985) Plant Cell Tissue Organ Culture 4, 183–197. Carbenicillin was used to kill A3144 after co-cultivation occurred. Transformed calli were selected on 5 mg/l phosphinotricine and 100 ug/ml kanamycin, and resistant calli were regenerated into plants. After induction of shoots and roots, the transformants were transferred to the greenhouse and grown until they flower. The flowers are examined, and they exhibit essentially the same phenotype as was observed for the transformed tobacco plants described in Example 10. This shows that the TA29 promoter is capable of directing the expression of the heterologous RNase T1 gene selectively in tapetum cells of plants other than tobacco, so as to render such other plants male-sterile.

EXAMPLE 12

Construction of a Chimaeric DNA Sequence of PTA29 and a Barnase Gene

Figure 8:
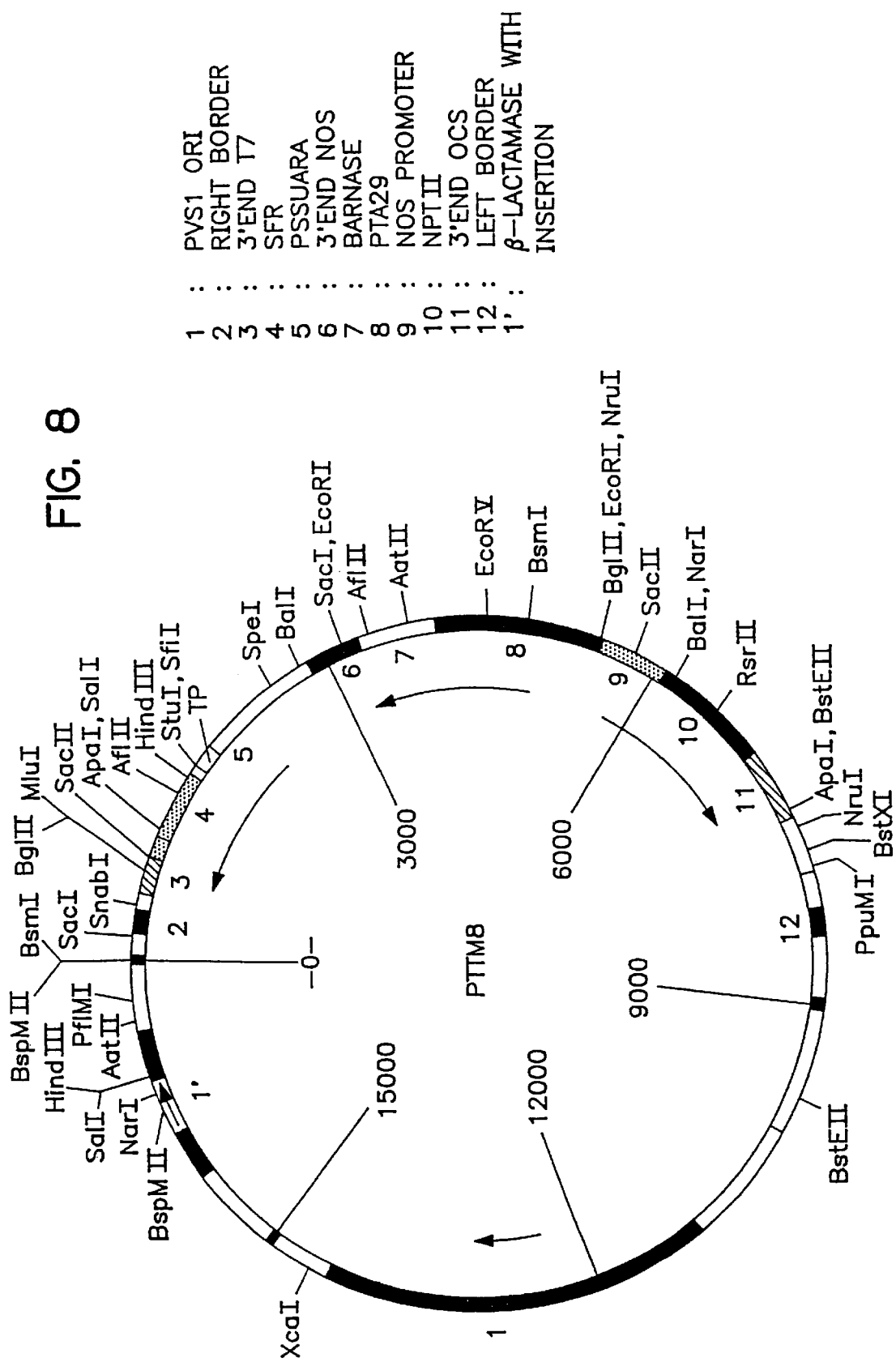
FIG. 8 shows a map of the vector pTTM8 of Example 12.

A plasmid named "pTTM8" shown in FIG. 8, was constructed by assembling the following well known fragments:

1. a vector fragment, including T-DNA border sequences derived from pGSC1700 (Cornelissen and Vandewiele (1989) NAR 17 (1) 19–29) and in which the β-lactamase gene (1' of FIG. 8) has been inactivated by insertion of a DNA sequence into its ScaI site;
2. the chimaeric sequence (no. 3) of Example 5, containing the PSSU promoter, the herbicide-resistance gene sfr and the 3' end of T-DNA gene 7;
3. the chimaeric sequence (no. 4) of Example 5, containing the PNOS promoter, the neo gene, and the 3' end of the octopine synthase gene; and
4. a chimaeric sequence, containing the PTA29 promoter cassette from Example 3, fused in frame with the Barnase gene from *Bacillus amiloliquefaciens* (Hartley and Rogerson (1972) Preparative Biochemistry 2, (3), 243–250) and the 3' end of the nopaline synthase gene of Example 9.

pTTM8 is a binary type T-DNA vector containing, within the T-DNA border sequences, three chimaeric sequences: PSSU-sfr and PNOS-neo which are markers DNAs with respectively PSSU and PNOS as second promoters; and PTA29-Barnase gene which is a male-sterility DNA under the control of PTA29 as a first promoter. Expression in tapetum cells of the male-sterility DNA under the control of the TA29 promoter will produce Barnase selectively in the tapetum cells so that Barnase will interfere with the metabolism of these cells.

EXAMPLE 13

Introduction of the Chimaeric DNA Sequence of Example 12 into Tobacco and Oilseed Rape As described in Example 11, a recombinant Agrobacterium strain was constructed by mobilizing pTTM8 (from Example 12) from *E. coli* into Agrobacterium C58C1 Rif$^R$ containing pMP90 (Koncz and Schell (1986) Mol. Gen. Genetics 204, 383–396). The resulting strain (named "A3135"), harboring pMP90 and pTTM8, is used for tobacco leaf disc transformation and for oilseed rape transformation. Transformed calli and shoots are selected using 5 mg/l phosphinothricin and 100 ug/ml kanamycin. That the Barnase gene is not expressed in the transformed herbicide-resistant calli and shoots is shown by their growth.

The transformed shoots are rooted, transferred to soil in the greenhouse and grown until they flower. The flowers of both the tobacco and oilseed rape are examined, and a phenotype is observed for the transformed plants that is essentially the same as the phenotype of the transformed tobacco plants described in Example 10. This shows that the TA29 promoter is capable of directing expression of the heterologous Barnase gene selectively in tapetum cells of the plants, thereby rendering the plants male-sterile.

EXAMPLE 14

Construction of a Chimaeric DNA Sequence of pTA29 and a Gene Encoding Papain

Figure 9A:
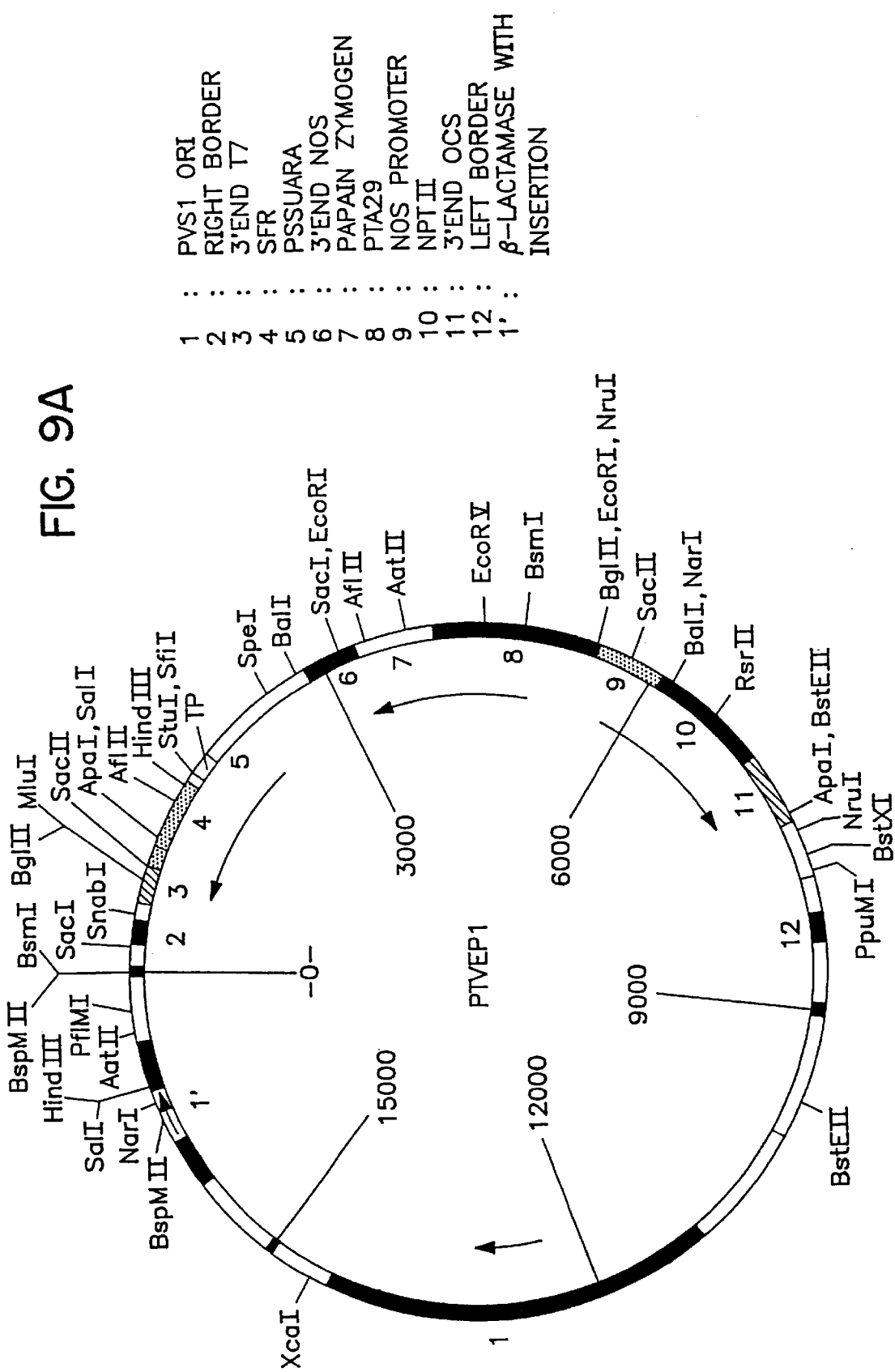
FIG. 9A shows a map of the vector pTVEP1 of Example 14.

A plasmid named "pTVEP1", shown in FIG. 9A, is constructed by assembling the following well known fragments:
1. a vector fragment, including T-DNA border sequences derived from pGSC1700 and in which the β-lactamase gene (1' of FIG. 9A) has been inactivated by insertion of a DNA sequence into its ScaI site;
2. the chimaeric sequence (no. 3) of Example 5, containing the PSSU promoter, the herbicide resistance gene sfr and the 3' end of T-DNA gene 7.
3. the chimaeric sequence (no. 4) of Example 5, containing the PNOS promoter, the neo gene and the 3' end of the octopine synthase gene; and
4. a chimaeric sequence, containing the PTA29 promoter cassette from Example 3, fused in frame with:
    a) a papain gene from *Carica papaya* fruit, encoding the papain zymogen which is a plant endopeptidase (Cohen et al (1986) Gene 48, 219–227) capable of attacking peptide, as well as ester, bonds; the following modifications are made in the DNA sequence of Cohen et al (1986) using site directed mutagenesis as described in Example 3:
        i. the nucleotide A, position-1 upstream of the first ATG codon, is mutated into nucleotide C in order to obtain a suitable NcoI cloning site; and
        ii. the GAA codons encoding glutamate at positions 47, 118, 135, respectively, are mutated into CAA codons encoding glutamine; and
    b) the 3' end of the nopaline synthase gene of Example 9.

pTVEP1 is a binary type T-DNA vector containing, within the T-DNA border sequences, three chimaeric sequences: PSSU-sfr and PNOS-neo which are marker DNAs encoding dominant selectable markers for plant transformations, under the control of respectively PSSU and PNOS as second promoters; and PTA29-Papain gene which is a male-sterility DNA under the control of PTA29 as a first promoter. Expression in tapetum cells of the male-sterility DNA under the control of the TA29 promoter will produce an endopeptidase (the papain zymogen) that will cleave proteins in the tapetum cells, thus leading to the death of these cells.

A plasmid named "pTVEP2", shown in FIG. 9B, is also constructed by assembling the following well known fragments:
1. a vector fragment, including T-DNA border sequences derived from pGSC1700 and in which the β-lactamase gene (1' of FIG. 9B) has been inactivated by insertion of a DNA sequence into the ScaI site;
2. the chimaeric sequence (no. 3) of Example 5, containing the PSSU promoter, the herbicide resistance gene sfr and the 3' end of T-DNA gene 7;
3. the chimaeric sequence (no. 4) of Example 5, containing the PNOS promoter, the neo gene, and the 3' end of the octopine synthase gene; and
4. a chimaeric sequence, containing the PTA29 promoter cassette of Example 3, fused in frame with:
    a) a papain gene from *Carica papaya* fruit, encoding the active protein of the papain zymogen; the following modifications are made in the DNA sequence of Cohen et al (1986), using site directed mutagenesis as described in Example 3:
        i. the AAT codon encoding Asn, upstream of the first Ile residue of the active protein, is mutated into a GAT codon, which provides a suitable EcoRV cloning site (GAT ATC). The EcoRV engineered site is fused directly to the pTA29 cassette in order to obtain a direct in frame fusion of the promoter with the sequence encoding the active protein of the papain zymogen; and
        ii. the GAA codons encoding glutamate at positions 47, 118, 135 respectively, are mutated into CAA codons encoding glutamine; and
    b) the 3' end of the nopaline synthase gene of Example 9.

pTVEP2, like pTVEP1, is a binary type T-DNA vector containing, within the T-DNA border sequences, three chimaeric genes: PSSU-sfr and PNOS-neo encoding dominant selectable markers for plant transformations; and PTA29-Papain gene which encodes an endopeptidase that will cleave proteins in the tapetum cells, thus leading to the death of these cells.

EXAMPLE 15

Introduction of the Chimaeric DNA Sequences of Example 14 into Tobacco and Oilseed Rape As described in Example 11, pTVEP1 and pTVEP2, are each mobilized from *E. coli* into separate Agrobacterium C58C1 Rif$^R$ carrying pMP90.

The resulting strains, harboring pMP90 with pTVEP1 and pMP90 with pTVEP2, are used to transform tobacco and oilseed rape following the procedures of Examples 11 and 13. That the papain genes are not expressed in transformed herbicide- and kanamycin-resistant calli, shoots and roots is shown by their growth.

The transformed plants are transferred into the greenhouse and grown in soil until they flower. The flowers of both the tobacco and oilseed rape are examined, and phenotypes are observed for the transformed plants that are essentially the same as the phenotype of the transformed tobacco plants described in Example 10. This shows that the TA29 promoter is capable of directing expression of the heterologous papain genes in pTVEP1 and pTVEP2 selectively in tapetum cells of the plants, thereby rendering the plants male-sterile.

EXAMPLE 16

Construction of a Chimaeric DNA Sequence of pTA29 and a Gene Encoding EcoRI

A plasmid named "pTVE63", shown in FIG. 10A, was constructed by assembling the following well known fragments:
1. a vector fragment, including T-DNA border sequences derived from pGSC1701A2 (European patent application 87/115985.1);
2. the chimaeric sequence (no. 3) of Example 5, containing the PSSU promoter, the herbicide-resistance gene sfr and the 3' end of T-DNA gene 7;
3. the chimaeric sequence (no. 4) of Example 5, containing the PNOS promoter, the neo gene and the 3' end of the octopine synthase gene;

4. a chimaeric sequence, containing the pTA29 promoter cassette of Example 3, fused in frame with:
   a) a gene encoding the EcoRI restriction endonuclease from an *E. coli* (Green et al (1981) J. Biol. Chem. 256, 2143–2153; Botterman and Zabeau (1985) Gene 37, 229–239) and capable of recognizing and cleaving the target sequence GAATTC on a double stranded DNA; the following modifications were made in the DNA sequence of Green et al (1981) using site directed mutagenesis as described in Example 3:
      i. the nucleotides of the ATG initiation codon were replaced by ATGCA, creating a NsiI site at the initiation codon and yielding the following nucleotide sequences:
         ATGCA,TCT,AAT . . . ; and
      ii. the Hind-HindIII fragment of the EcoRI gene cloned in pEcoR12 (Botterman and Zabeau, 1985) was cloned into the pMAC5-8 site directed mutagenesis vector; and
   b) the 3' end of the nopaline synthase gene of Example 9; and
5. a gene encoding an EcoRI methylase under the control of its natural promoter (Botterman and Zabeau (1985) Gene 37, 229–239) which is capable of inhibiting the activity of EcoRI in *E. coli* or Agrobacterium, in order to overcome potential leaky expression of the EcoRI gene in microorganisms.

pTVE63 is a binary type T-DNA vector containing, within the T-DNA border sequences, three chimaeric sequences: PSSU-sfr and PNOS-neo which are marker DNAs under the control of respectively PSSU and PNOS as second promoters; and PTA29-EcoRI gene which is a male-sterility DNA under the control of PTA29 as a first promoter. Expression of the male-sterility DNA under the control of the TA29 promoter in tapetum cells will produce the EcoRI restriction endonuclease which will cleave double stranded DNA at the GAATTC sites (see for review of type II restriction modification systems: Wilson (1988) TIG 4 (11), 314–318) of the tapetum cells, thus leading to the death of these cells.

A plasmid named pTVE62, shown in FIG. 10B, was also constructed by assembling the following well known fragments:

1. a vector fragment, including T-DNA border sequences derived from pGSC1701A2;
2. the chimaeric sequence (no. 3) of Example 5, containing the PSSU promoter, the herbicide-resistance gene sfr and the 3' end of T-DNA gene 7;
3. the chimaeric sequence (no. 4) of Example 5, containing the PNOS promoter, the neo gene and the neo 3' end of the octopine synthase gene;
4. a chimaeric sequence, containing the pTA29 promoter cassette of Example 3, fused in frame with a gene fragment encoding the transit peptide of the Mn-superoxide dismutase ("Mn-SOD") which is a NcoI-PstI fragment of a HpaI-HindIII fragment from pSOD1 (Bowler et al (1989) Embo J. 8, 31–38); the following modifications were made in the DNA sequence of Bowler et al using site directed mutagenesis as described in Example 3:
   i. the AA nucleotides located upstream at position −2 and −1 of the ATG initiation codon were changed to CC nucleotides creating a NcoI site at the initiation codon and yielding the following nucleotide sequences:
      CCATGGCACTAC
          NcoI
   ii. the T,TCG,CTC, nucleotides located immediately downstream of the processing site of the transit peptide were changed to C,TGC,AGC, creating a PstI site behind the processing site and yielding the the following nucleotide sequences:

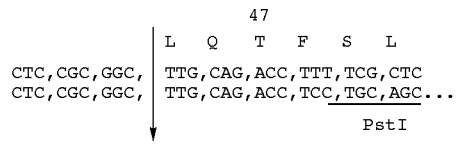

in which the arrow indicates the processing site of the transit peptide sequence and the upper line the aminoacid sequence corresponding with the Mn-SOD coding sequence; the NcoI-PstI fragment was also fused in frame with a gene encoding the EcoRI restriction endonuclease from *E. coli* (Greene et al (1981) J. Biol. Chem. 256, 2143–2153; Botterman and Zabeau (1985) Gene 37, 229–239) and capable of recognition and cleavage of the target sequence GAATTC on a double stranded DNA, as found in pTVE63; and
   b) the 3' end of the nopaline synthase gene of Example 9; and
5. a gene encoding the EcoRI methylase under the control of its natural promoter (Botterman and Zabeau, 1985) which is capable of inhibiting the activity of EcoRI in *E. coli* or Agrobacterium, in order to overcome potential leaky expression of the EcoRI gene in microorganisms, this gene being inserted into the vector fragment outside the border sequences.

pTVE62 is a binary type T-DNA vector containing, within the border sequences, three chimeric sequences: PSSU-sfr and PNOS-NPTII which are marker DNAs under the control of respectively PSSU and PNOS as second promoters; and pTA29-transit peptide-EcoRI endonuclease gene which is a male-sterility DNA having PTA29 as a first promoter and a transit peptide-encoding sequence between them. Expression of the male-sterility DNA under the control of the TA29 promoter in tapetum cells will produce a restriction endonuclease which will be targeted into the mitochondria of the tapetum cells and cleave the double stranded DNA at the GAATTC sites in such cells. This will lead to the death of these cells.

EXAMPLE 17

Introduction of the Chimaeric DNA Sequences of Example 16 into Tobacco and Oilseed Rape As described in Examples 11 and 15, pTVE62 and pTVE63, were mobilized from *E. coli* into Agrobacterium C58C1 Rif$^R$ carrying pMP90. The resulting strains, harboring pTVE62 with pMP90 and pTVE62 (with pMP90, were used to transform tobacco and are used to transform oilseed rape following the procedures described in Examples 11 and 13. That the EcoRI endonuclease genes were not expressed in transformed herbicide- and kanamycin-resistant calli, shoots and roots is shown by their growth.

The transformed plants are transferred into the greenhouse and grown in soil until they flower. The flowers of both the tobacco and oilseed rape are examined, and phenotypes are observed for the transformed plants that are essentially the same as of the transformed tobacco plants described in Example 10. This shows that the TA29 promoter is capable of directing expression of the heterologous EcoRI endonuclease gene selectively in the tapetum cells of the plants transformed with pTVE62 and pTVE63, thereby rendering the plants male-sterile.

Needless to say, this invention is not limited to the transformation of any specific plant(s). The invention relates to any plant, the nuclear genome of which can be transformed with a male-sterility DNA under the control of a first promoter that can direct expression of the male-sterility DNA selectively in the plant's stamen cells, whereby the plant can be both self-pollinated and cross-pollinated. For example, this invention relates to plants such as potato, tomato, oilseed rape, alfalfa, sunflower, cotton, celery, onion, corn, soybean, tobacco, brassica vegetables and sugarbeet.

Also, this invention is not limited to the specific plasmids and vectors described in the foregoing Examples, but rather encompasses any plasmids and vectors containing the male-sterility DNA under the control of the first promoter.

Furthermore, this invention is not limited to the specific promoters described in the foregoing Examples, such as the TA29 promoter, but rather encompasses any DNA sequence encoding a promoter capable of directing expression of the male-sterility DNA selectively in stamen cells. In this regard, this invention encompasses the DNA sequence of the TA29 promoter of FIG. 1A, as well as any equivalent DNA sequences, such as that of the TA13 promoter of FIG. 3B and the TA26 promoter of FIG. 3C, which can be used to control the expression of the male-sterility DNA selectively in tapetul cells of a plant. Indeed, it is believed that the DNA sequences of the TA29, TA26 and TA13 promoters can be modified by: 1) replacing some codons with others that code either for the same amino acids or for other amino acids; and/or 2) deleting or adding some codons; provided that such modifications do not substantially alter the properties of the encoded promoter for controlling tapetum-specific expression of a male-sterility.

In addition, this invention is not limited to the specific male-sterility DNAs described in the foregoing Examples but rather encompasses any DNA sequence encoding a first RNA, protein or polypeptide which disturbs significantly the metabolism functioning and/or development of a stamen cell in which it is produced, under the control of the first promoter.

Also, this invention is not limited to the specific marker DNAs described in the foregoing Examples but rather encompasses any DNA sequence encoding a second RNA, protein or polypeptide which confers on at least a specific plant tissue or specific plant cells, in which such DNA sequence is expressed, a distinctive trait cared to such a specific plant tissue or specific plant cells in which such DNA sequence is not expressed.

What is claimed is:

1. A plant comprising cells having a nuclear genome transformed with a foreign DNA, said foreign DNA comprising:
   a) a male-sterility DNA encoding a protein or polypeptide capable, when produced in an anther cell of a plant, of significantly disturbing at least one of metabolism, functioning and development of said anther cell; and
   b) a first promoter which directs gene expression selectively in stamen cells of a plant, and causes gen e expression in anther cells of said plant,
   said male-sterility DNA being in the same transcriptional unit as, and under the control of, said first promoter; wherein said anther cells of said plant are killed or disabled by expression of said male-sterility DNA in said anther cells of said plant, so as to render said plant incapable of producing fertile male gametes.

2. The plant of claim 1, in which said first promoter causes gene expression in anther epidermal cells of said plant, wherein said anther epidermal cells of said plant are killed or disabled by expression of said male-sterility DNA in said anther epidermal cells of said plant, so as to render said plant incapable of producing fertile male gametes.

3. The plant of claim 1, in which said first promoter causes gene expression in tapetum cells of said plant, wherein said tapetum cells of said plant are killed or disabled by expression of said male-sterility DNA in said tapetum cells of said plant, so as to render said plant incapable of producing fertile male gametes.

4. The plant of claim 3, wherein said first promoter is from an endogenous plant gene which encodes an mRNA from which a cDNA of at least 365 bp in length can be prepared which shares at least about 92% sequence similarity with the TA29 cDNA of FIG. 2, the DNA of FIG. 3A between positions 1477 and 2592, or the TA13 cDNA of FIG. 3B.

5. The plant of claim 3, wherein said first promoter is from an endogenous plant gene which encodes an mRNA from which the TA29 cDNA of FIG. 2 or the TA13 cDNA of FIG. 3B can be prepared.

6. The plant of claim 3, wherein said first promoter comprises the 31 nucleotide sequence of FIG. 3A, upstream of nucleotide position 1477.

7. The plant of claim 3, wherein said first promoter comprises the nucleotide sequence of FIG. 3A upstream of nucleotide position 1477.

8. The plant of claim 3, wherein said first promoter comprises the nucleotide sequence of FIG. 3A from nucleotide position 16 to nucleotide position 1476.

9. The plant of claim 4, wherein said foreign DNA further comprises an untranslated leader sequence with the following nucleotide sequence:
   TACAACATCATCACTCAAAT-
   CAAAGTTTTTACTTAAAGAAATTAGCTAAA.

10. The plant of claim 4, wherein said foreign DNA further comprises an untranslated leader sequence with the following nucleotide sequence:
    ACAACATCATCACTCAAATCAAAGTTTT-
    TACTTAAAGAAATTAGCTACC.

11. The plant of claim 4, wherein said DNA comprises the ClaI-NcoI fragment of plasmid pMB3, DSM 4470.

12. The plant of claim 1, wherein said male-sterility DNA encodes a ribonuclease.

13. The plant of claim 12, wherein said male-sterility DNA encodes Rnase T1.

14. The plant of claim 3, wherein said male-sterility DNA encodes a ribonuclease.

15. The plant of claim 4, wherein said male-sterility DNA encodes a ribonuclease.

16. The plant of claim 5, wherein said male-sterility DNA encodes a ribonuclease.

17. The plant of claim 8, wherein said male-sterility DNA encodes a ribonuclease.

18. The plant of claim 10, wherein said male-sterility DNA encodes a ribonuclease.

19. The plant of claim 1, wherein said male-sterility DNA encodes a barnase.

20. The plant of claim 3, wherein said male-sterility DNA encodes a barnase.

21. The plant of claim 4, wherein said male-sterility DNA encodes a barnase.

22. The plant of claim 5, wherein said male-sterility DNA encodes a barnase.

23. The plant of claim 8, wherein said male-sterility DNA encodes a barnase.

24. The plant of claim 10, wherein said male-sterility DNA encodes a barnase.

25. The plant of claim 1 or 3, wherein said male-sterility DNA encodes: a Dnase; a protease; a glucanase; a lipase, a lipid peroxidase; a cell wall inhibitor; or a bacterial toxin.

26. The plant of claim 1, wherein said male-sterility DNA encodes an enzyme which catalyzes synthesis of a phytohormone.

27. The plant of claim 1, wherein said foreign DNA further comprises a first DNA encoding a transit peptide capable of transporting said protein or polypeptide into a chloroplast or mitochondrion of said stamen cells; said first DNA being in the same transcriptional unit as said male-sterility DNA and said first promoter and between said male-sterility DNA and said first promoter.

28. The plant of any one of claims 1, 3, 12 or 14 wherein said foreign DNA further comprises:
  (c) a marker DNA encoding a marker RNA, protein or polypeptide which, when present at least in a specific tissue or in at least specific cells of said plant, renders said plant easily separable from other plants which do not contain said marker RNA, protein or polypeptide in said specific tissue or specific cells; and
  (d) a second promoter capable of directing expression of said marker DNA at least in said specific tissue or specific cells; said marker DNA being in the same transcriptional unit as, and under the control of, said second promoter.

29. The plant of claim 28, wherein said marker DNA encodes a protein inhibiting or neutralizing action of an herbicide.

30. The plant of claim 29, wherein said marker DNA is an herbicide resistance gene.

31. The plant of claim 30, wherein said marker DNA is a gene conferring resistance to a glutamine synthetase inhibitor.

32. The plant of claim 31, wherein said marker DNA is a gene conferring resistance to phosphinothricin.

33. The plant of claim 32, wherein said marker DNA is a sfr or sfrv gene.

34. The plant of claim 29, wherein said marker DNA is a gene encoding a modified target enzyme for an herbicide which (1) has a lower affinity for the herbicide and (2) is a modified 5-enolpyruvylshikimate-3 phosphate synthase as a target for glyphosate, or a modified glutamine synthetase as a target for a glutamine synthetase inhibitor.

35. The plant of claim 28, wherein said marker DNA is a gene encoding a protein or a polypeptide conferring a color to at least said specific tissue or specific cells; a gene encoding a protein or a polypeptide conferring a stress tolerance to said plant, a gene encoding a protein or a polypeptide conferring a disease or pest resistance, a gene encoding a *Bacillus thuringiensis* endotoxin that confers insect resistance, or a gene encoding a bactericidal peptide that confers a bacterial resistance.

36. The plant of claim 28, wherein said second promoter is: a constitutive promoter or a wound-inducible promoter.

37. The plant of claim 29, wherein said second promoter is a constitutive promoter or a promoter which directs gene expression selectively in plant tissue having photosynthetic activity.

38. The plant of claim 37, wherein said second promoter is a CaMV 35S promoter or a ribulose bisphosphate carboxylase SSU promoter.

39. The plant of claim 30, wherein said second promoter is a constitutive promoter or a promoter which directs gene expression selectively in plant tissue having photosynthetic activity.

40. The plant of claim 39, wherein said second promoter is a CaMV 35S promoter or a ribulose bisphosphate carboxylase SSU promoter.

41. The plant of claim 32, wherein said second promoter is a constitutive promoter or a promoter which directs gene expression selectively in plant tissue having photosynthetic activity.

42. The plant of claim 41, wherein said second promoter is a CaMV 35S promoter or a ribulose bisphosphate carboxylase SSU promoter.

43. The plant of claim 33, wherein said second promoter is a constitutive promoter or a promoter which directs gene expression selectively in plant tissue having photosynthetic activity.

44. The plant of claim 43, wherein said second promoter is a CaMV 35S promoter or a ribulose bisphosphate carboxylase SSU promoter.

45. The plant of claim 28, which further comprises a second DNA encoding a transit peptide capable of transporting said second protein or polypeptide into a chloroplast or mitochondria of at least said specific tissue or specific cells; said second DNA being in the same transcriptional unit as said marker DNA and said second promoter and between said marker DNA and said second promoter.

46. The plant of claim 45, wherein said marker DNA is an herbicide resistance gene.

47. The plant of claim 45, wherein said marker DNA is a sfr or a sfrv gene.

48. A plant of claim 1, wherein said foreign DNA is the T-DNA of pTTM4 of FIG. 6, the T-DNA of pTTM6 of FIG. 7A, the T-DNA of pTTM6A of FIG. 7B, the T-DNA of pTTM8 of FIG. 8, the T-DNA of pTVEP1 of FIG. 9A, the T-DNA of pTVEP2 of FIG. 9B, the T-DNA of pTVE62 of FIG. 10B or the T-DNA of pTVE63 of FIG. 10A.

49. A cell of a plant of any one of claims 1, 3, 12 or 14, wherein said cell comprises said foreign DNA.

50. A seed of a plant of any one of claims 1, 3, 12 or 14, wherein said seed comprises said foreign DNA.

51. A process for obtaining a seed of a seed-forming plant, wherein said process comprises:
  a) cross-pollinating i) the plant of claim 1 which is male-sterile, and ii) a male-fertile plant; and
  b) obtaining seed from said male-sterile plant.

52. The process of claim 51 wherein said first promoter in said male-sterile plant is a promoter which directs gene expression selectively in stamen cells of a plant, and causes gene expression in tapetum cells of said plant.

53. The process of claim 52, wherein said first promoter is the promoter of the TA29 gene of FIG. 3A.

54. The process of claim 52, wherein said male-sterility DNA in said male-sterile plant encodes a ribonuclease.

55. The process of claims 52 or 53, wherein said male-sterility DNA in said male-sterile plant encodes a barnase.

56. A process for producing a seed of a plant, wherein said process comprises:
  a) cross-pollinating i) the plant of claim 28 which is male-sterile, and ii) a male-fertile plant which does not contain said marker DNA or said second promoter;
  b) eliminating male-fertile plants on the basis of absence of expression of said marker DNA in said male-fertile plants;
  c) obtaining seeds of said pollinated male-sterile plants.

57. The process of claim 56 wherein said male-fertile plants are eliminated prior to said cross-pollination.

58. The process of claim 56, wherein said male-fertile plants are eliminated after said cross-pollination.

59. A process for producing a seed of a plant, wherein said process comprises:
   a) cross-pollinating i) the plant of claim 29 which is male-sterile, and ii) a male-fertile plant which does not contain said marker DNA or said second promoter;
   b) applying said herbicide to the plants for eliminating male-fertile plants;
   c) obtaining seeds of said pollinated male-sterile plants.

60. The process of claim 59, wherein said herbicide is applied prior to said cross-pollination.

61. The process of claim 59, wherein said herbicide is applied after said cross-pollination.

62. The process of claim 59, wherein said herbicide is a phosphinothricin.

63. The process of claim 59, wherein said marker DNA is a sfr or sfrv gene.

64. A process for producing a seed of a plant, wherein said process comprises:
   a) cross-pollinating i) the plant of claim 39 which is male-sterile, and ii) a male-fertile plant which does not contain said marker DNA or said second promoter;
   b) applying said herbicide to the plants for eliminating male-fertile plants;
   c) obtaining seeds of said pollinated male-sterile plants.

65. The process of claim 64, wherein said herbicide is applied prior to said cross-pollination.

66. The process of claim 64, wherein said herbicide is applied after said cross-pollination.

67. The process of claim 64, wherein said herbicide is a phosphinothricin.

68. The process of claim 64, wherein said marker DNA is an sfr or sfrv gene.

69. The plant of claim 34 wherein said glutamine synthetase inhibitor is phosphinothricin.

70. The plant of claim 28, wherein said second promoter is a promoter which directs gene expression selectively in plant tissue having photosynthetic activity.

71. The plant of claim 70, wherein said second promoter is a promoter which directs gene expression selectively in leaf cells, petal cells or seed cells.

* * * * *